(12) United States Patent
Mok et al.

(10) Patent No.: US 8,090,742 B2
(45) Date of Patent: *Jan. 3, 2012

(54) PATIENT DIRECTED SYSTEM AND METHOD FOR MANAGING MEDICAL INFORMATION

(75) Inventors: Megan Wai-Han Mok, Pacifica, CA (US); Arthur Douglas Jopling, San Rafael, CA (US); R. David Holvey, Pacifica, CA (US); Joel D. Mattox, Saratoga, CA (US)

(73) Assignee: Peoplechart Corporation, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/628,876

(22) Filed: Dec. 1, 2009

(65) Prior Publication Data

US 2010/0094658 A1 Apr. 15, 2010

Related U.S. Application Data

(63) Continuation of application No. 10/159,489, filed on May 31, 2002, now Pat. No. 7,647,320.

(60) Provisional application No. 60/349,883, filed on Jan. 18, 2002.

(51) Int. Cl.
*G06F 17/30* (2006.01)
(52) U.S. Cl. .................. 707/770; 705/2; 705/3
(58) Field of Classification Search .................. 707/609, 707/705, 770, 790, 802, 821, 966; 705/2, 705/3, 44, 51; 715/248, 764
See application file for complete search history.

(56) References Cited

U.S. PATENT DOCUMENTS

| | | | | |
|---|---|---|---|---|
| 5,832,450 A * | 11/1998 | Myers et al. | | 705/3 |
| 6,347,329 B1 * | 2/2002 | Evans | | 709/202 |
| 6,611,846 B1 * | 8/2003 | Stoodley | | 707/740 |
| 6,651,060 B1 * | 11/2003 | Harper et al. | | 1/1 |
| 2001/0041991 A1 * | 11/2001 | Segal et al. | | 705/3 |
| 2001/0053986 A1 | 12/2001 | Dick | | 705/3 |
| 2002/0004727 A1 | 1/2002 | Knaus et al. | | 705/3 |
| 2003/0115084 A1 * | 6/2003 | Gage | | 705/3 |

OTHER PUBLICATIONS

Jerome H. Carter, MD, Electronic Medical Records, 2001 American College of Physicians.*
Lin et al., A Unified Multimedia Database System to Support Telemedicine, 1998 IEEE, pp. 183-192.*
http://www.personalmd.com/press34_article.shtml, 9 pages, Jun. 8, 2000.

* cited by examiner

*Primary Examiner* — Fred I Ehichioya
(74) *Attorney, Agent, or Firm* — Ladas & Parry, LLP

(57) ABSTRACT

A system and method is provided for the management of a patient's medical records by a central data repository under the direction of the patient and enabled by an entity managing records on behalf of the patient. Medical records from a plurality of the patient's healthcare providers, including past and present healthcare providers, are maintained in this central repository in a way that provides a centralized, comprehensive, and accessible medical history of the patient, as well as a comprehensive organizational structure across all records. An embodiment has the patient directed central repository as the hub in a hub-and-spoke arrangement, where each spoke goes to one of the patient's healthcare providers, both past and present. The patient's medical records are collected from all the patient's healthcare providers, then classified, stored, and organized for use by the patient, healthcare providers, and any other authorized individuals. The records in the repository can be sorted and/or selected in several different ways and displayed to the patient or to his designated medical care providers, and to certain patient designated third parties.

92 Claims, 27 Drawing Sheets

DOCUMENTID: 455 — 820
Medications & Allergies — 822
810
Mary Jane Adams, MemberID: 532 — 824, 826
814

MEDICATION SUMMARY

Patient Name *Mary Jane Adams*
Pharmacy _____
Account Number _____
Phone _____

| DATE | MEDICATION - DOSE - # | INSTRUCTION | RF | LF | OK |
|---|---|---|---|---|---|
| 2/18/77 | Imitrex tabs 50mg #9 | | 0 | 11/26/97 | PH |
| 1/15/98 | Imitrex tabs 50 mg. #9 | | 6 | 12/15/97 358-2715 | PH |
| 3-2-98 | Imitrex 50 mg #9 | 358-2715 | 3 | | DT |
| 4/24/98 | Ogen .625mg, TQD | 358-2715 | 6 | | H |
| 4-20-99 | Imitnex 50mg #9 | MJA Ams 358-2715 | 7 | 5-28-98 | CS |
| 10-26-98 | Ogen .625mg | 358-2715 | 5 | 7-26-98 | CS |
| 10-26-98 | Progesterone #30 | 292-6192 | 12 | | CS |
| 1-5-99 | Ogen .625mg #45 1/2 gd need appt (6/12) | 339-0363 | 0 | | YM |
| 6/17/99 | Ogen .625 mg QD #14 | 358-2915 | | | PN |
| 7/2/99 | gen. Ogen 1.25 mg. TQD #30 | 358-2915 | 6 | | PN |
| 7/26/99 | Celebrex 100mg #810 #60 | 358-2915 | 2 | new | PN |
| 8/17 | (9) K Amber catag IF cella) | | | | |
| 5/15/00 | Ambien 10mg#30 | 3582915 | 0 | | AV |
| 5/18/00 | Imitrox 50mg #9 | | 2 | | A |

Author: Jane Doe, M.D.; Date: 5/18/2000    Specialization: Internal Medical/Family Practice/Primary Care
Peoplechart (415) 362-8600

| | 912 | 914 | 916 | 918 | 910 | 920 | 922 |

CLASSIFICATIONS OF PAGE TYPE (BY MEDICAL CATEGORY)

| Index ID | CMR Sub-Sections | Timeline Sections | MS Sub-Sections | Description | Codes |
|---|---|---|---|---|---|
| 1 | 1 | 1 | 1 | Medications & Allergies | MED |
| 2 | 1 | 1 | 1 | Medication Refills & Logs | REF |
| 3 | 2 | 2 | 2 | Immunizations | IMU |
| 4 | 3 | 3 | NM | Patient Intake Forms | PIF |
| 5 | 4 | 4 | 3 | Physical Exams | PHX |
| 6 | 5 | 5 | 4 | Progress Notes-Outpatient (typed) | PN1 |
| 7 | 5 | 5 | 4 | Progress Notes-Outpatient (untyped) | PN0 |
| 8 | 6 | 6 | 5 | Consultants-Outpatient (typed) | CN1 |
| 9 | 6 | 6 | 5 | Consultants-Outpatient (untyped) | CN0 |
| 10 | 7 | 7 | 6 | Operative Notes | SUR |
| 11 | 8 | 8 | 7 | ER Reports | ERR |
| 12 | 9 | 9 | 8 | Hospital Summaries: Discharge Summary | HDS |
| 13 | 9 | 9 | 8 | Hospital Summaries: Admitting History & Physical | HHP |
| 14 | 9 | 9 | 8 | Hospital Summaries: Consultants-Inpatient | HCN |
| 15 | 9 | 9 | 8 | Hospital Summaries: Progress Notes-Inpatient | HPN |
| 16 | 9 | 9 | 8 | Hospital Summaries: Other | HOT |
| 17 | 10 | 10 | 9 | EKGs | EKG |
| 18 | 11 | 11 | 10 | Imaging: X-rays or Radiologic | XRY |
| 19 | 11 | 11 | 10 | Imaging: MRI | MRI |
| 20 | 11 | 11 | 10 | Imaging: Ultrasounds | UTR |
| 21 | 11 | 11 | 10 | Imaging: CAT or CT scans | CAT |
| 22 | 11 | 11 | 10 | Imaging: Mammograms | MAM |
| 23 | 11 | 11 | 10 | Imaging: Other | IOT |
| 24 | 12 | 12 | 11 | Special Tests | SPT |
| 25 | 13 | 13 | 12 | Labs & Cultures: CBC &/or Chemistry | LBC |
| 26 | 13 | 13 | 12 | Labs & Cultures: Protime | LPR |
| 27 | 13 | 13 | 12 | Labs & Cultures: Other | LOT |
| 28 | 14 | 14 | 13 | Therapy Notes | THR |
| 29 | 15 | 15 | NM | Billing & Insurance | BIN |
| 30 | 16 | CM | NM | Other: Administration | OAD |
| 31 | 16 | CM | NM | Other: Record Release | ORR |
| 32 | 16 | CM | NM | Other: Title Pages | OTP |
| 33 | 16 | CM | NM | Other: Duplicate Pages | ODP |
| 34 | 16 | CM | NM | Other: Irrelevant Pages | OIR |
| 35 | 16 | CM | NM | Other: Unclassified Pages | OUN |

FIG. 15

PEOPLECHAR
*"Information you can live with"*

Combined Medical Records

Find record pages
by Document Log
by Document Timeline

View by Sections
Table of Contents
Patient Inputs
Document Log
 Sorted by Date
 Sorted by Category
 Sorted by Specialization
Document TI
Clinical Pages
Medications & Allergies
Immunizations
Patient Intake Forms
Physical Exams
Progress Notes
Consultants
Operative Notes
ER Reports
Hospital Summaries
EKGs
Imaging
Special Tasks
Labs & Cultures
Therapy Notes
Billing & Insurance
Other

View Entire Report
Combined Medical Records

Mary Jane Adams — Patient Inputs | Medical Records | Medical Summary | Administration email  fax  Help

Document Log Sorted By Category

[Hide Private] — 936

| Private | Document ID | Date | Record Provider | Page category-Sort Key | Author | Specialization |
|---|---|---|---|---|---|---|
| ☑ | 455 | 5/18/2000 | Dr Jane Doe | Medications & Allergies | Jane Doe, M.D. | Internal Medicine |
| ☐ | 456 | 11/26/1997 | Dr Jane Doe | Medications & Allergies | Jane Doe, M.D. | Internal Medicine |
| ☐ | 480 | 2/13/1995 | Dr Jane Doe | Patient Intake Applications | Jane Doe, M.D. | Internal Medicine |
| ☐ | 457 | 6/15/1999 | Dr Jane Doe | Physical Exams | Jane Doe, M.D. | Internal Medicine |
| ☐ | 458 | 6/15/1999 | Dr Jane Doe | Physical Exams | Jane Doe, M.D. | Internal Medicine |
| ☐ | 459 | 6/15/1999 | Dr Jane Doe | Physical Exams | Jane Doe, M.D. | Internal Medicine |
| ☐ | 460 | 6/15/1999 | Dr Jane Doe | Physical Exams | Jane Doe, M.D. | Internal Medicine |
| ☐ | 463 | 11/10/1997 | Dr Jane Doe | Physical Exams | Jane Doe, M.D. | Internal Medicine |
| ☐ | 464 | 11/10/1997 | Dr Jane Doe | Physical Exams | Jane Doe, M.D. | Internal Medicine |
| ☐ | 465 | 11/10/1997 | Dr Jane Doe | Physical Exams | Jane Doe, M.D. | Internal Medicine |
| ☐ | 466 | 11/10/1997 | Dr Jane Doe | Physical Exams | Jane Doe, M.D. | Internal Medicine |
| ☐ | 468 | 11/30/1996 | Dr Jane Doe | Doctor's Notes: Progress Notes (untyped) | Jane Doe, M.D. | Internal Medicine |
| ☐ | 470 | 10/30/1996 | Dr Jane Doe | Doctor's Notes: Progress Notes (untyped) | Jane Doe, M.D. | Internal Medicine |
| ☐ | 471 | 10/30/1996 | Dr Jane Doe | Doctor's Notes: Progress Notes (untyped) | Jane Doe, M.D. | Internal Medicine |
| ☐ | 472 | 10/30/1996 | Dr Jane Doe | Doctor's Notes: Progress Notes (untyped) | Jane Doe, M.D. | Internal Medicine |
| ☐ | 452 | 10/25/1999 | Dr Jane Doe | Doctor's Notes: Progress Notes (untyped) | Jane Doe, M.D. | Internal Medicine |
| ☐ | 453 | 8/17/1999 | Dr Jane Doe | Doctor's Notes: Progress Notes (untyped) | Jane Doe, M.D. | Internal Medicine |
| ☐ | 454 | 7/6/1999 | Dr Jane Doe | Doctor's Notes: Progress Notes (untyped) | Jane Doe, M.D. | Internal Medicine |
| ☐ | 461 | 2/10/1998 | Dr Jane Doe | Doctor's Notes: Progress Notes (untyped) | Jane Doe, M.D. | Internal Medicine |
| ☐ | 462 | 3/18/1997 | Dr Jane Doe | Doctor's Notes: Progress Notes (untyped) | Jane Doe, M.D. | Internal Medicine |
| ☐ | 467 | 2/6/1997 | Dr Jane Doe | Doctor's Notes: Progress Notes (untyped) | Jane Doe, M.D. | Internal Medicine |

PATIENT DIRECTED SYSTEM AND METHOD FOR MANAGING MEDICAL INFORMATION

CROSS-REFERENCE TO RELATED APPLICATIONS

This application is a continuation of U.S. patent application Ser. No. 10/159,489, filed on May 31, 2002, which claims priority from and incorporates by reference in its entirety U.S. Provisional Application Ser. No. 60/349,883 titled "A System And Method For Managing Medical Information," filed on Jan. 18, 2002.

FIELD OF THE INVENTION

The invention relates generally to the field of medical records management and in particular to the collection, organization, presentation, and distribution of a patient's medical records.

BACKGROUND OF THE INVENTION

Having a complete set of medical records significantly improves the quality of health care for a patient by establishing a patient's medical baseline and indicating patterns in the patient's medical history. These records provide information impacted by time and by the diversity of medical view points and knowledge gained from clinical tests. Having a comprehensive set of data that goes back in time and that is inclusive of observations and findings from multiple providers who have seen or treated the patient over time makes a difference in the quality of the information used to accurately diagnose and treat medical problems. This is especially true for medical problems in the early stages of development. Patient records, when consolidated and complete, often show identifiable patterns of symptoms, diagnoses, treatments and responses to those treatments over the life of the patient. When new health issues arise, or an old one recurs, the information and patterns contained in the medical records can help guide health professionals in making new diagnoses and in their choices for treatments. Each patient's baseline medical information is unique. Many people exhibit unusual readings on some medical tests as part of their normal healthy baseline state, even though those same readings might be considered unhealthy when considered in isolation. In the context of the patient's past history, these unusual readings become part of the patient's baseline, and the repetition of those unusual readings over time is not a major concern. However, in the absence of the patient's historical baseline information, these unusual test results could provoke misunderstandings or over-reactions from doctor(s) not familiar with the patient's history. The risk of medical errors can be significantly reduced by providing patient-specific information to doctors currently diagnosing or treating the patient about the patient's adverse effects of past treatments, allergic reactions to certain drugs, and general disposition to certain diseases or health conditions. In addition, part of a patient's medical history can include their family medical history. Historical family records of medical conditions can help determine a patient's level or risks for certain medical conditions, such as heart disease, diabetes, and breast cancer, and can alert health care providers when increased screening and other tests are advisable.

In the past, when a patient generally had one or a handful of doctors for most of his life, the doctor(s) more often had records and knowledge of the patient's complete medical history. In today's world, a number of economic forces and trends in health care are contributing to the increasing fragmentation of patient records across multiple providers, and to increasing discontinuity in the knowledge of the patient's medical history by the patient's doctors over time. Examples of these trends include the increasing frequency with which patients change medical insurance and jobs, move residences, and are being referred to health care specialists. In addition, it is now more common for patients to consult with multiple doctors and specialists for treatment alternatives and second opinions. On the provider side of the health care industry, there is a growing trend toward increased specialization on the part of doctors. Also, in response to economic pressures and wide-spread disruptions in the health care industry caused by business insolvency, poor operating results, and by increasing frustrations with unpopular reimbursement policies and cost-cutting practices of hospitals, Health Maintenance Organizations (HMOs), and other health care groups, doctors have become more resolved to close practices or switch their allegiance to business practices and affiliations. When they do switch, patients often need to find new doctors or organizations to provide them care. Today's patient typically sees many more healthcare providers over his lifetime than was the case in previous generations.

Each healthcare provider is concerned with the maintenance and/or restoration of the health of the body and/or mind of the patient. The health care provider may be one person (e.g., sole practitioner), a group of persons (e.g., a family clinic), or an organization (e.g., hospital or medical university) that for legal and billing reasons, is the author, owner, and custodian of only that portion of a patient's medical records corresponding to the diagnosis or treatment that the healthcare provider provides to the patient. For today's patient, there is very seldom a single provider who would have all the records of the patient's other providers, past and present. Moreover, because patient's medical records are typically paper-based records, the healthcare provider incurs overhead costs in maintaining and storing them. This creates an economic incentive for each healthcare provider to try to minimize the records it keeps to only those records pertaining to the portion of the patient's care that the healthcare provider itself has provided. When the healthcare provider requires access to other portions of the patient's medical records (i.e., information about the patient authored by other healthcare providers), requesting-physicians typically only request and retrieve from these other health care providers medical records that are of immediate relevance to them. Hence only a subset, rather than a complete set, of a patient's medical records are kept by a health care provider in order to minimize the additional storage and other administrative costs. For the same economic reasons, a healthcare provider typically discards a patient's medical records, after the patient becomes inactive under that provider's care for a legally specified time, e.g., 5 to 7 years.

From the record sending side, there are problems in performing the transfer of medical records between healthcare providers. There is also an economic disincentive and therefore a reluctance or a slow reaction for the healthcare provider holding the patient's medical records to transfer copies of a patient's records to other providers because the costs of retrieval, copying, and mailing are traditionally born by the sending-physician as a common courtesy to the receiving-physician. To help keep these costs down, the tasks of administering, copying, and mailing record copies are often performed only during slow periods or during lulls in other activities of the medical office staff. The relatively low priority assigned to providing copies of medical records often results in long delays between the request for and the delivery of patient records, even when disclosure is legally authorized and record copies required to be released.

Upon receipt, the receiving-providers often need to reorganize the paper records according to their own system of record-keeping. While the increased use of electronic medical records (EMRs) over paper-based records has reduced the storage cost, paper-based records are still prevalent. Over 80% of patients' medical record information still exist in paper formats. Doctors continue to make handwritten notes of their diagnoses and treatments. In addition, today when records are kept in electronic form in an Electronic Medical Record (EMR) system, records are still commonly transmitted between doctors in hard copy, paper-format. This is true even when both doctors have access to different EMR systems because such systems are rarely compatible with each other. When the transfer of patient information is between one computer application and another, the computer applications maintaining the electronic medical records typically differ between health care providers. So, if it is deemed necessary to convert paper records into electronic format for information consolidation and processing, the receiving-provider would have to bear the cost of converting records to electronic format, including record storage costs and the ongoing costs of creating scanned images of paper-based records. Rather than converting records from sending-providers into electronic format, or from sending-providers' electronic format to paper-based and then to the receiving-providers' electronic format, today's common practice is for recipient-providers to simply review the paper copies of records received and file them away with the rest of the patient's paper-based records providers.

Thus, because each healthcare provider typically keeps their own medical records of the patient and because there is little actual sharing or records between healthcare providers, the result is a fragmentation of a patient's medical records across the multiple healthcare providers. In effect each healthcare provider becomes a part of a puzzle of the patient's medical history, and no healthcare provider sees the whole picture. This fragmentation of information about the patient is further exacerbated by the patient's increasing use of specialists and increasing need to switch health insurance plans and healthcare providers in order to pursue better care or to reduce cost of the premium. The increase in providers seen in the context of little real sharing of patient's medical records across providers also results in increasing incidence of redundant tests and of treatments that are done in lieu of each new doctor have timely access to a patient's complete medical records. In addition, as the Institute of Medicine summarized in a 1999 report, lack of communication and information on patient medical conditions and history of drug reactions can be cited as a key reason that medical errors result in thousands of otherwise preventable deaths each year. On the provider side, there are economic pressures for providers to switch health affiliations due to poor business results or business insolvency of their current practice or affiliations or due to increasing frustration with reimbursement policies and cost-cutting practices of hospitals, HMOs and other health care groups.

FIG. 1 illustrates the fragmentation puzzle of a patient's medical records of the prior art. A patient has typically many healthcare providers over the patient's life, e.g., hospitals A and H, doctors B, C, D, and E, and other provides F and G (e.g., providers of Chiropractic or Homeopathic medicine). Doctors B and C illustrate by overlap area 110 the case when two healthcare providers share some, but not all their medical records. If two healthcare providers share all their records then for the purposes of this application, they are considered to be the same healthcare provider. In addition a patient may keep her own files.

FIG. 2 is a block diagram of an example flow of a patient's medical records among different healthcare providers of the prior art, that results in the fragmentation puzzle of FIG. 1. FIG. 2 illustrates that a partial transfer, or in some cases no transfer, of a patient's records from one healthcare provider to another causes more and more fragmentation of a patient's medical history over a patient's lifetime. While in this example, for illustration purposes, medical records are described as transferred between health care providers, the records are actually transferred from one health care provider's medical record repository or filing system to another health care provider's medical record repository or filing system. In this example, a patient begins with a general practitioner 110, e.g., a pediatrician, when the patient was a child. The patient then has general practitioner 112 as an adult. General practitioner 112 thinking that it was too long ago, decides not to request past medical records from general practitioner 110 and instead relies on a patient interview to fill in the patient's medical history. As a patient's memory is often fuzzy and a poor substitute for clinical information, general practitioner 112 gets an incomplete picture of the patient's childhood medical history. General practitioner 112 may send the patient to a specialist 114, e.g., a surgeon for an appendectomy. The specialist 114 gets some of the patient's medical records from general practitioner 112 (path 113a) and may also request other historical records from general practitioner 110 (path 118). The specialist 114 creates her own records and transfers all or most of these initial records, but not all ongoing records, back to general practitioner 112 (path 113b). The patient continues to see the specialist 114, at times without the General Practitioner 112. The ongoing updates by the specialist 114, after the initial introduction, are usually not managed and so any new information accumulated on the patient would most likely not be communicated back to General Practitioner 112. General practitioner 112 meanwhile continues to add new records as he continues to care for the patient. When the patient moves to a new general practitioner 120, for example, because of moving, changing jobs or switching to a health plan to which general practitioner 112 is not affiliated, the new provider will need access to the patient's medical history. As illustrated, the possible paths for general practitioner 120 to get a complete set of medical records is becoming complex. To get a complete medical history of the patient, general practitioner 120 needs medical records from general practitioner 110 (path 131), general practitioner 112 (path 130) and specialist 114 (path 132). However, to reduce costs and because of the delay in getting the records, general practitioner 120 may only request some "needed" records from general practitioner 112 (path 130) and no records from general practitioner 110 (path 131) or specialist 114 (path 132). If general practitioner 120 refers the patient to specialist 122, then specialist 122 has many paths, i.e., 121a, 134, and from which he may need medical records. However, specialist 122 may, to cut costs, only request the patient's medical records from general practitioner 120 (path 121a). Note that at this point no single provider necessarily has complete records on all patient medical care. Thus as this example indicates, as a patient goes from healthcare provider to healthcare provider, the patient's medical records often get more and more fragmented. Further, at some point, practitioners will discard the patient's medical records and vital information may be forever lost and will not be available at a critical time.

Several prior art systems have tried to solve the fragmentation problem by providing a centralized computer storage area available to the patient for storage of some of a patient's medical records. However, these prior art systems only store a small subset of a patient's medical history. Most examples of these prior art systems are Electronic Medical Record (EMR) systems that have scope and function limited to the portion of the patient's records corresponding to only that provider's care. One system allows a patient or his doctor to fax in to the central repository copies of the patient's medical records under their control. Some minimal organization of the scanned images is done manually by the patient, e.g., putting certain images in a patient's emergency folder and the rest in a general folder. As the number of images gets large, this very limited organization of the scanned images does not allow for timely retrieval of a relevant subset by a doctor currently treating a patient. In addition, because the patient, not a medical records technician, medical professional, or health service entity, selects what is to be placed in the emergency folder, some of relevant data may be omitted. Thus this system has both the disadvantages of a very incomplete patient history and limited usefulness of the images because the patient is forced to make decisions about the relevancy of certain medical information.

A patient's health is best served by a complete or nearly complete set of medical records with a comprehensive organizational structure used throughout. In contrast, prior art systems only provide a small subset of the patient's medical records within organizational structures that are likely to be inadequate to the needs and the time pressures of a healthcare provider currently diagnosing and treating the patient: the vast majority of the patient's medical records remain fragmented over the rest of the patient's many past and present healthcare providers. Prior art systems which provide the ability to consolidate a patient's medical records from the past do not provide meaningful or comprehensive organization for the patient's consolidated medical records. What is needed is a method and system that manages a complete or nearly complete set of a patient's medical records that allows easy retrieval and meaningful display of relevant information.

SUMMARY OF THE INVENTION

The present invention includes a system and a method for the collection, organization, and distribution of a patient's medical records by a central data repository under the direction of the patient. Medical records from a plurality of the patient's healthcare providers, including past and present healthcare providers, are maintained in this central repository, thus providing a comprehensive, organized, and accessible medical history of a patient.

An exemplary embodiment has a patient-directed central data repository and a set of processes that enable the patient to be the hub in a hub-and-spoke arrangement, where each spoke goes to one of the patient's healthcare providers, both past and present. The patient's medical records, past and present, and any updates thereunto, from one or more of the patient's healthcare providers are collected, classified and stored in the central data repository At the patient's authorization, healthcare providers can gain access to the central repository and view the patient's consolidated medical records. The system which stores the records in the central data repository provides classification schema and capabilities that enable the record pages to be sorted and prioritized in numerous meaningful ways. The sorted medical records and descriptive information about the entire record collection can be displayed to both the patient and/or the healthcare provider currently advising and/or treating the patient and/or other entities designated by the patient. The system also automatically organizes the medical record documents in such a way that facilitates the generation of reports that can then be readily distributed via fax, email, hardcopy and/or CD-ROM to the patient or patient's designated entities.

One embodiment of the present invention includes a method for organizing patient's medical records authored by multiple healthcare providers. Two or more documents, comprising part of the patient's medical records, are categorized according to a categorization system and stored in a storage area of a central repository, where access to the central storage area must be authorized by the patient. An ordered set of the categorized documents is retrieved from the central storage area using at least one criterion of a plurality of predetermined criteria. In addition the ordered set may be displayed via a Web browser or distributed in hard copy format.

Another embodiment of the present invention includes a method for selecting and sorting two or more documents from the patient's complete medical records according to selected document categories and various sort criteria. In addition, the sorted documents can be displayed via a Web browser rather than distributed via fax, email or hard copy format]

Another embodiment of the present invention includes a method for a patient accessing his/her own medical records originated from multiple healthcare providers. First, the documents of the patient's medical records are collected from both past and present healthcare providers. The documents are then categorized according to a categorization system having more than two categories and stored in a central storage area on a computer system, where the storage area is under direct or indirect control of the patient. An example of indirect control is a service provider that directly controls the central storage area, but is directed by the patient, or the patient's legal representative, on what information can be viewed and accessed and by whom. Lastly, a document is retrieved from the storage area according to a selection criterion, where the selection criterion is based on the categorization system. Optionally, the selected document is displayed to the patient or the patient distributes the document via fax or email or directs a service provider to distribute the document via fax, email, or send in hardcopy or CD-ROM format through traditional mail.

An aspect of the present invention, includes a method for a patient accessing his/her medical records originated by multiple healthcare providers. First, the patient's medical records are collected from the healthcare providers. Next, documents of the patient's medical records are categorized according to a categorization system, and the categorized documents are stored in the patient directed central computer storage area. A document log of some or all of the categorized documents is then displayed to the patient.

Another aspect of the present invention includes a system for centrally managing a patient's medical records originating from multiple healthcare providers. The system includes: a collection service module for collecting the patient's medical records from the healthcare providers; a computerized categorization system for categorizing each medical record, where the categorization system is the same for all of the patient's healthcare providers; a patient directed central computer storage area for storing the categorized medical records; and a retrieval module for retrieving ordered or sorted documents, where the ordered documents are arranged using at least one criterion of two or more criteria, where the criteria are based on the computerized categorization system.

Another embodiment of the present invention includes a method of centrally managing a patient's medical records originated by multiple healthcare providers. First, the patient's medical records, including paper-based documents, are collected from the patient's past and present healthcare providers. Next, each page of the paper-based documents is classified using classes of a classification system common across all the patient's healthcare providers. Each page of the paper-based documents is converted to an electronic image and stored in a computer readable medium, where third party access to the computer readable medium is authorized by the patient or his legal representative. An organized subset of said electronic images is retrieved using at least one selection criterion of a plurality of selection criteria, and displayed to a patient designated entity.

In yet another embodiment of the present invention a system for centrally managing patient's medical records originated by multiple healthcare providers is provided. The system includes: a backend server for receiving the patient's medical records from the patient's healthcare providers, where each document of the patient's medical records is categorized using the backend server; a database connected to the backend server for storing the categorized documents, where access to the categorized documents is controlled directly or indirectly by the patient or his legal representative; and a Web server connected to the backend server and to a client system, where the Web server processes a search request initiated by the client system for a select set of one or more document(s) out of all the stored categorized documents.

A further aspect of the present invention includes a method in a computer system for displaying a document log of the medical records of a patient. A table is displayed that includes multiple rows, where each row includes multiple columns, and where a column includes one or more cells associated with a category. Document ID data, which identifies a document in the patient's medical records, is displayed in a cell of a row.

Another aspect of the present invention includes a method, using a computer, for commenting on a medical record by a patient. First, an electronic image of said medical record is searched for using a category assigned to the medical record. The electronic image is stored in a database, where access to the electronic image is controlled by said patient. Next, a patient's comments and/or a provider's comments are associated with the electronic image and stored in the database. When the electronic image is recalled the comment is also recalled and displayed concurrently with the electronic image.

Another aspect of the present invention includes a method in a computer system for displaying a document timeline of documents in a patient's medical records. A first axis is displayed having sequential calendar time units, and a second axis is displayed listing the documents organized by medical category. For a particular document, there is an indication on the first axis of a calendar time unit having the date of creation and the name of the author of the particular document.

Yet another aspect of the present invention includes a method in a computer system for displaying a progress note timeline of multiple progress notes in a patient's medical records. A first axis is displayed indicating sequential calendar time units, and a second axis is displayed indicating the total number of progress notes per calendar time unit.

An embodiment of the present invention includes a method for a doctor using a patient's medical records, including clinical pages, stored in a patient directed computer storage area. First, the doctor selects a category that's of relevance from the list of multiple categories that could be used to categorize each clinical page. Next, a subset of the clinical pages is retrieved from the computer storage area, where the subset includes those clinical pages belonging to the category and not designated private by the patient. An "Availability" factor is calculated as a ratio of the number of clinical pages in the subset to the total number of clinical pages categorized with that category. Lastly, the Availability factor is displayed on the title page under the category for use by the doctor in evaluating the completeness of the subset.

Another embodiment of the present invention includes a method for a doctor using a patient's medical records, including clinical pages from a healthcare provider, stored in a patient directed computer storage area. First, the doctor selects a category of the multiple categories classifying the clinical pages. Next, a subset of the clinical pages belonging to the category is retrieved from the computer storage area. A "Source" factor is calculated as the ratio of a number of clinical pages in the subset obtained directly from the healthcare provider (as opposed to indirectly from the patient) to the total number of clinical pages in the subset. The source factor is then displayed to the doctor for use in evaluating reliability of the subset.

These and other embodiments, features, aspects and advantages of the invention will become better understood with regard to the following description, appended claims and accompanying drawings.

BRIEF DESCRIPTION OF THE DRAWINGS

FIG. 8 is an example of a user interface for entering the request for medical records of multiple providers (historical and current) of a given patient;

FIG. 10A is an example of a user interface for a system of categorizing a scanned page;

FIG. 10B is an example of a user interface for a system of cross-categorization, i.e., adding an additional category to an already categorized page or making edits to the categorization of a scanned page.

FIG. 11 shows an example of an electronic image with the categories added to the header and footer of the scanned page from FIG. 10A;

FIG. 12 is an example of a window of a physical exam summary page of a patient's medical records;

FIG. 15 is an example of a page listing the medical sub-categories representing various types of page (Page Type by Medical Category) found in a patient's medical record file and the order of presentation of particular tab sections for two reports that display record pages along these medical sub-categories of an embodiment of the present invention;

FIG. 16 is an example of a user interface allowing the designating of some of a patient's medical records as "Private";

FIG. 17 is an example of a document log sorted by medical sub-categories (page type), an aspect of the present invention;

FIG. 18 is an example of a document timeline for the documents in FIG. 17, an embodiment of the present invention;

FIGS. 20-1 to 20-7 show the database structure of an embodiment of the present invention.

DETAILED DESCRIPTION OF THE INVENTION

In the following description, numerous specific details are set forth to provide a more thorough description of the specific embodiments of the invention. It is apparent, however, to one skilled in the art, that the invention may be practiced without all the specific details given below. In other instances, well known features have not been described in detail so as not to obscure the invention.

Figure 2:
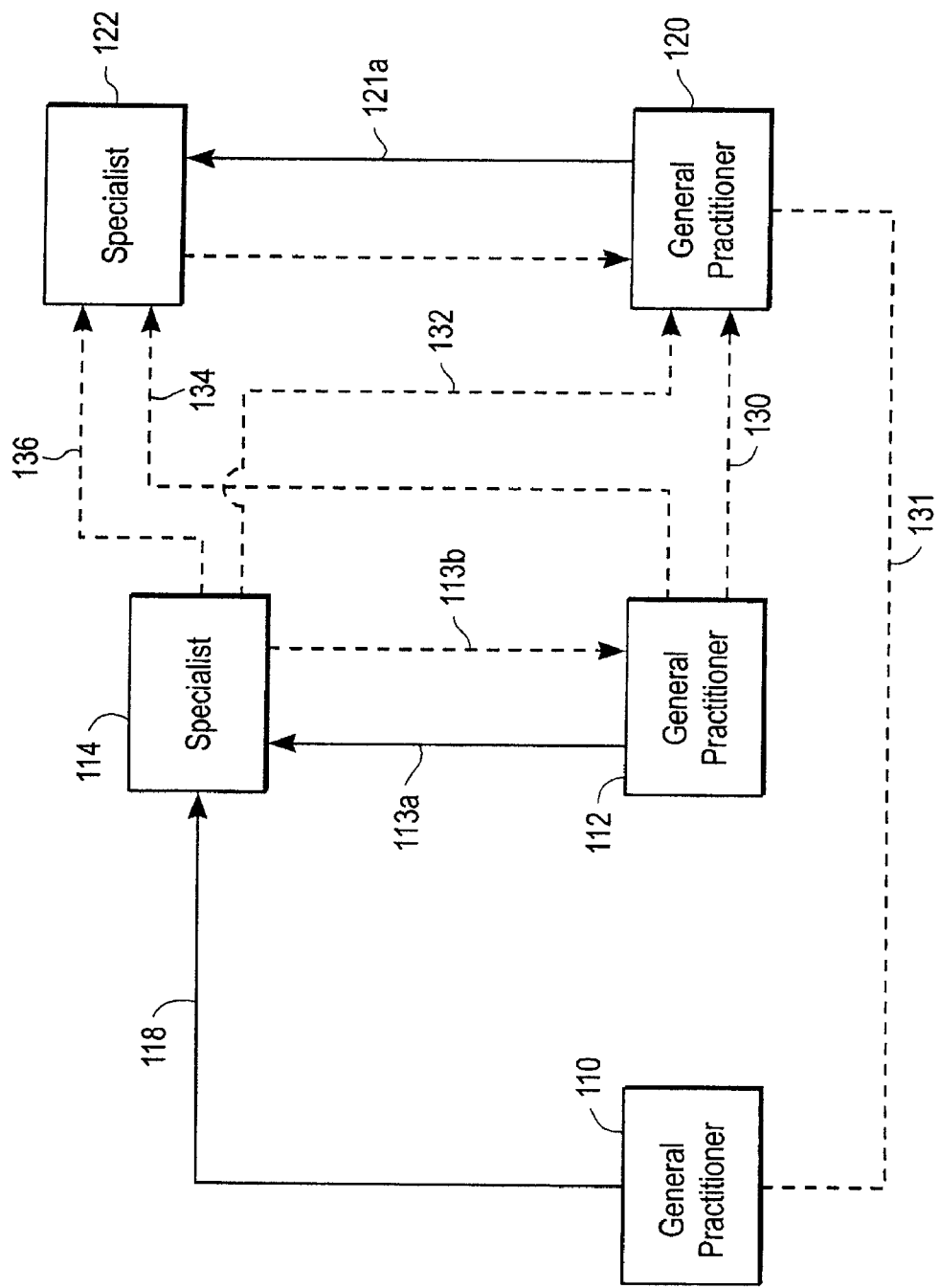
FIG. 2 is a block diagram of an example flow of a patient's medical records among different healthcare providers of the prior art, that results in the fragmentation puzzle of FIG.
Figure 3:
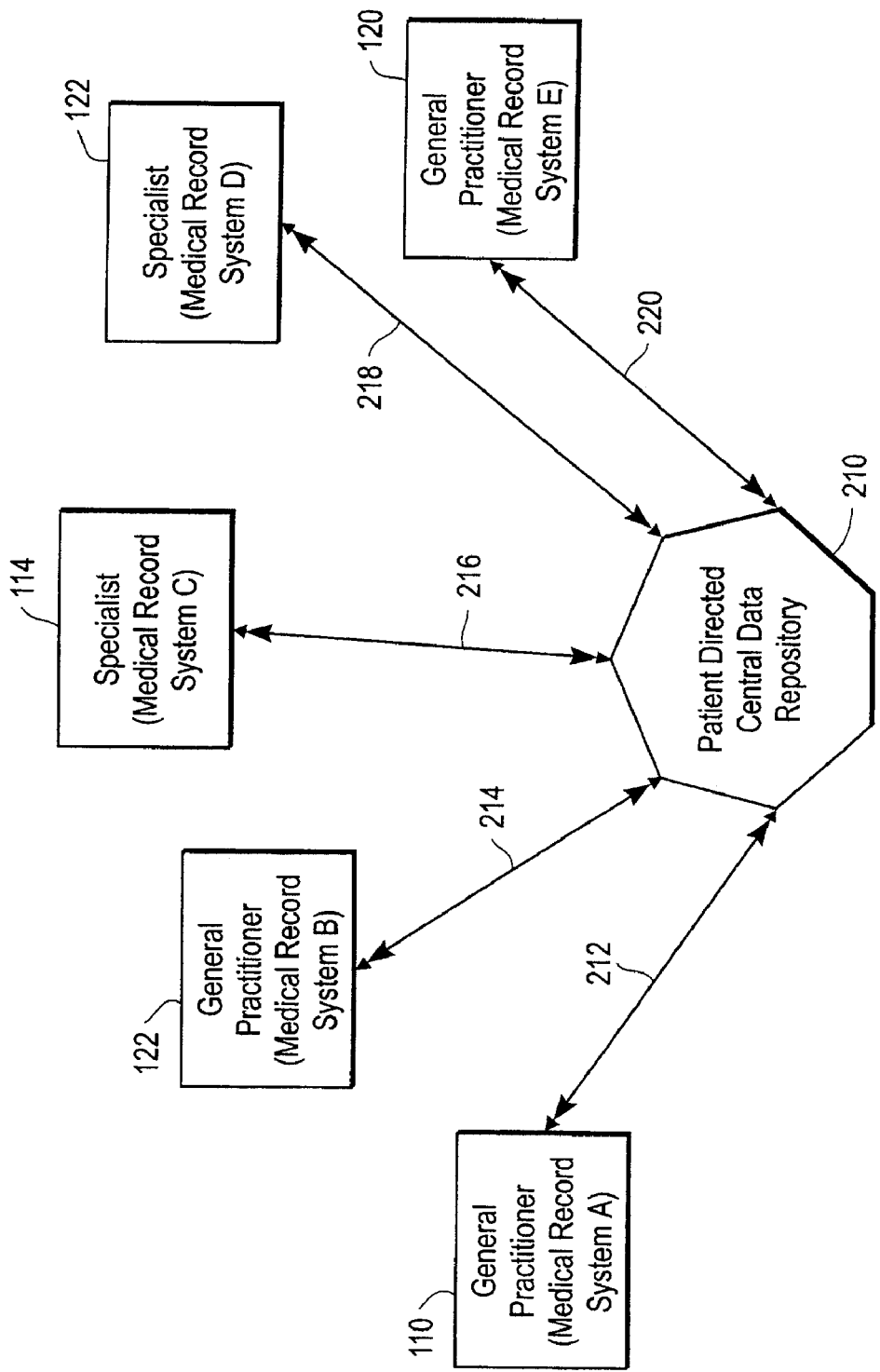
FIG. 3 is a block diagram illustrating the hub and spoke flow of a patient's medical records between different healthcare providers medical record systems and a patient's central data repository of one embodiment of the present invention.

FIG. 3 is a block diagram illustrating the hub and spoke flow of a patient's medical records between different healthcare providers medical record systems and the patient's central data depository of one embodiment of the present invention. The example of FIG. 3 uses the same healthcare providers as FIG. 2. The different healthcare provider medical records systems are shown in parentheses, as the records are actually transferred from one healthcare provider system to another healthcare provider system. The patient either has a central data repository himself that he directly controls or has a service provider (or another person or organization) having a central data repository for him, that the patient indirectly controls (i.e., the service provider must have the patient's explicit or implicit permission before any of the patient's medical records can be shown to a third party). Both of these central data repositories of a patient's medical records are called, herein, a patient directed central data depository 210 or "central data depository", as the patient or his legal representative has direct or indirect control on who has access to his medical information.

In the example of FIG. 3, a patient's childhood doctor is general practitioner 110, e.g., a pediatrician like in FIG. 2. However, unlike FIG. 2 the patient directed central data repository 210 does contain a complete copy of all of the patient's medical records authored by general practitioner 110. When patient 210 changes doctors to general practitioner 112, general practitioner 112 gets any of patient's past medical records, e.g., those kept by general practitioner 110, from the central data repository 210 rather than a past healthcare provider's medical record system. Copies of the patient's medical records generated by general practitioner 112 are also transferred to the central data repository 210. When the patient goes to specialist 114, specialist 114 uses the central data repository 210 for past medical records e.g., medical records kept by general practitioner 110 or current medical records, e.g., medical records kept by general practitioner 112. Similarly, when the patient changes health plans and gets a new general practitioner 120 and a new specialist 122, these doctors need only access the central data repository 210 to get any necessary medical records of the patient. Duplications and gaps in documentation are reduced by the current doctor being able to see a list of what's available in this central data repository 210. Thus the hub and spoke arrangement of FIG. 3 significantly simplifies the information flow given in FIG. 2, and significantly reduces or eliminates the fragmentation of a patient's medical records across the different healthcare providers.

Figure 1:
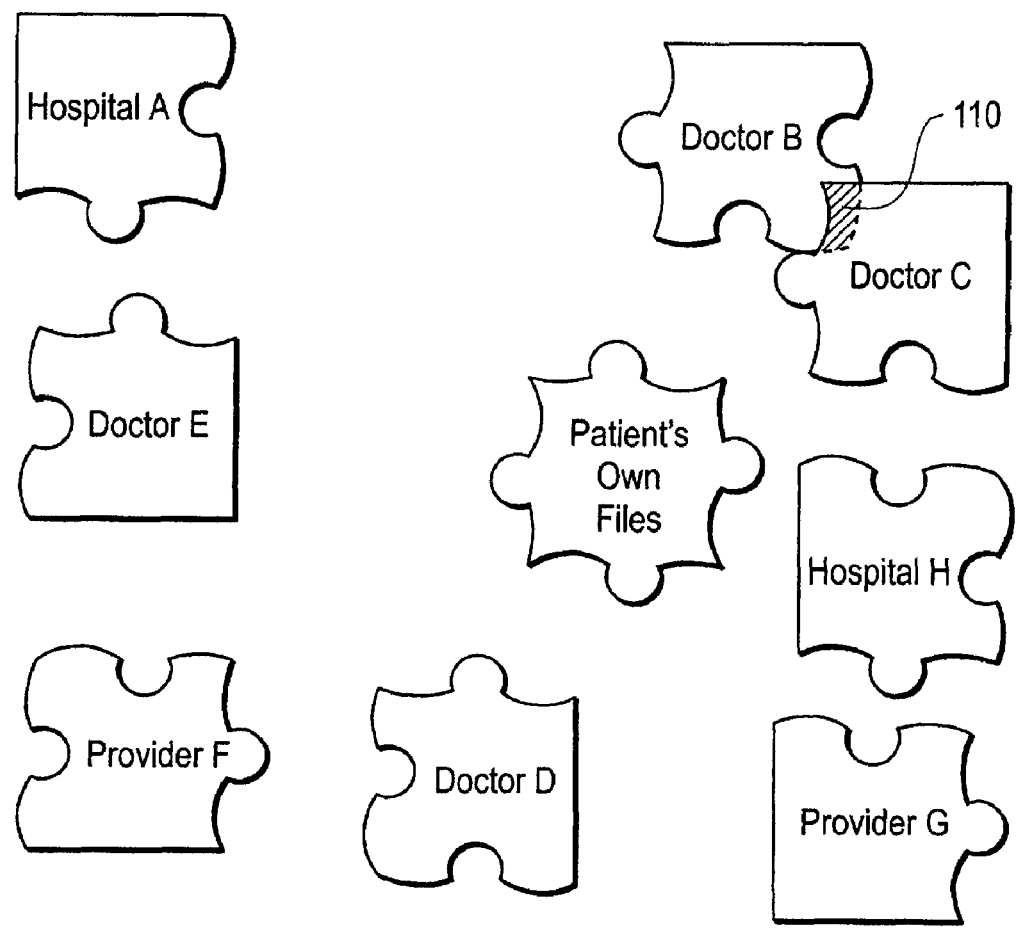
FIG. 1 illustrates the fragmentation puzzle of a patient's medical records of the prior art.
Figure 4:
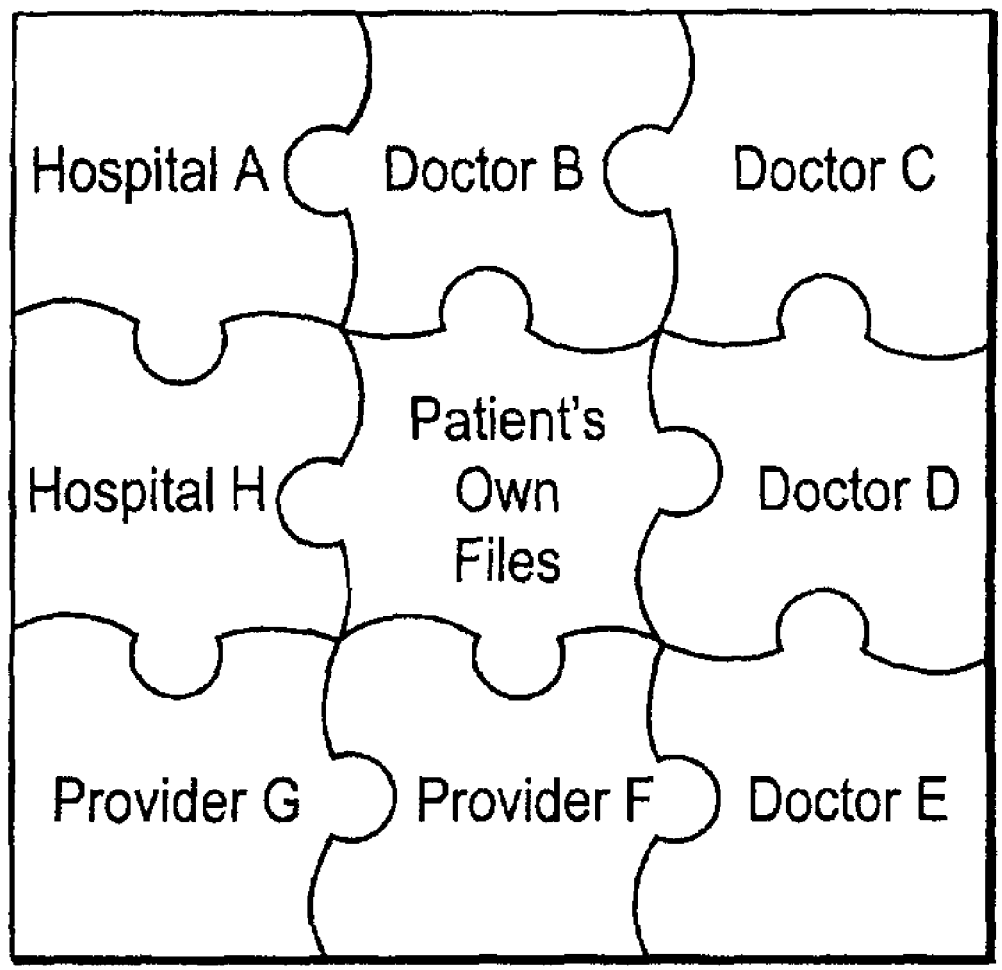
FIG. 4 shows the results of a consolidation of medical records from the multiple healthcare providers of FIG. 1 into a patient directed central data repository.

FIG. 4 shows the results of a consolidation of medical records from the multiple healthcare providers of FIG. 1 into a patient directed central data repository. Besides the major advantage of having a complete set of medical records available to the patient and his healthcare providers, duplicate records can be removed and the various pieces of a patient's medical history can be organized in a coherent and consistent fashion.

While the retrieval and consolidation of a patient's medical records into one central data repository is a necessary condition in using the patient's medical history effectively, such a collection is not sufficient. Unless the voluminous number of documents in a patient's medical records are adequately organized and presented, there is a small chance that a relevant subset of the collection of documents can be retrieved and displayed in a timely and relevant manner for use by a doctor currently diagnosing and treating the patient. Thus categorizing or classifying of each document in a patient's medical history is another necessary condition in using the patient's medical history effectively. One or more of the categories or classes is then used during the retrieval to order a part of or all of the collected documents, and a relevant subset for presentation is selected from the ordered documents based on a filtering criteria. For example, if a doctor's notes of the collection of documents are ordered chronologically by date of creation, then only the notes over the past year may be displayed.

The term "document", as used herein, comprises a text or word processing file, an image file (e.g., pdf, jpeg, bmp), a page of a paper-based or electronic medical record, a film (e.g. X-Ray), a video or audio clip, a multimedia file, or a page of any softcopy or hardcopy of information related to the patient. The term "medical" is not limited to the medical field, but includes dental, pharmaceutical, optometric, audiological, chiropractic, physical rehabilitation, mental health, insurance and contact information relating to the patient, and/or any other traditional or non-traditional healing fields. The term "clinical" refers to any medical information (historical or current), provider or test-result based or information provided by the patient, that can be used as data for proper diagnosis and treatment of the patient.

Figure 5:
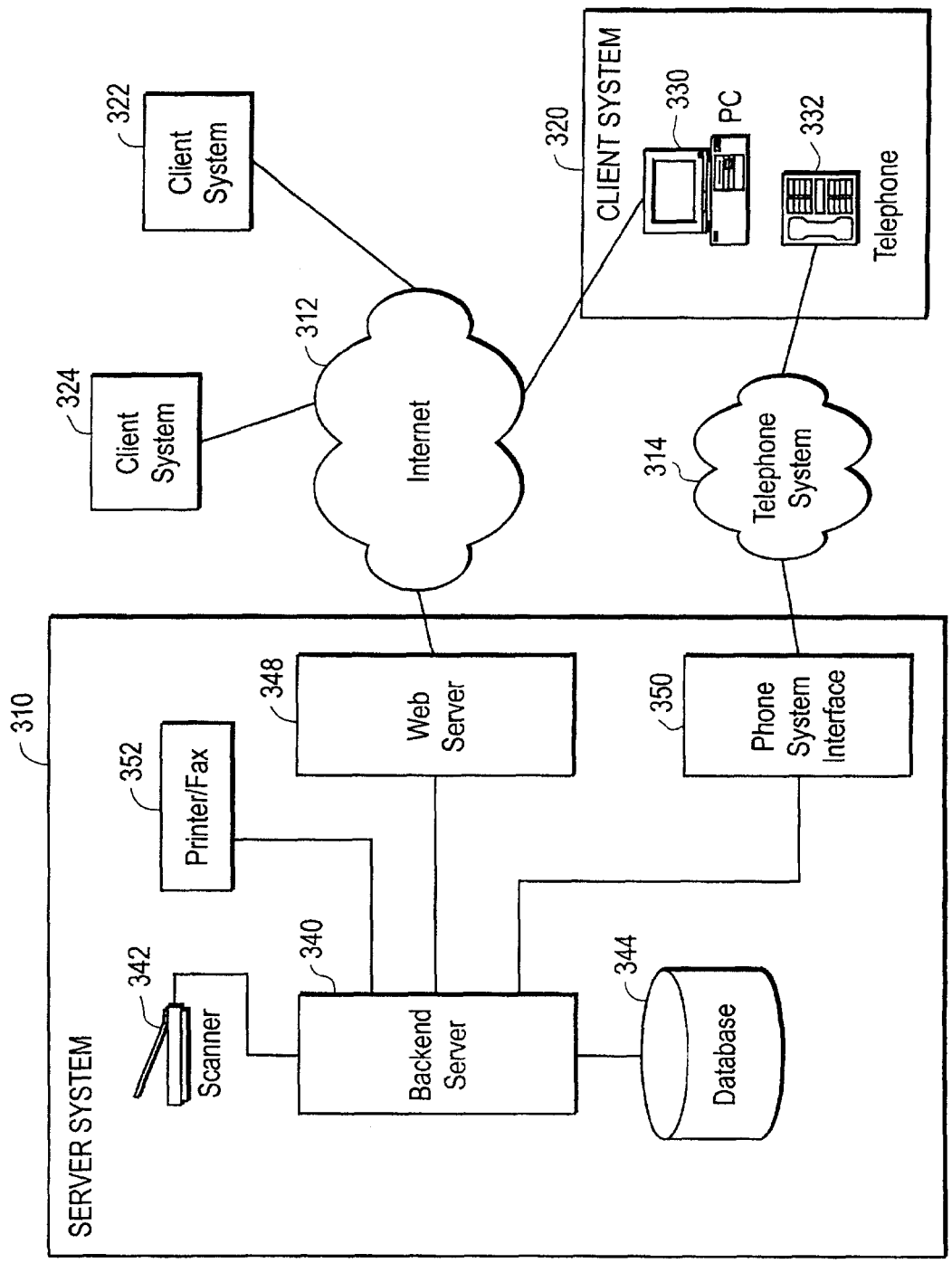
FIG. 5 is a client-server architecture of one embodiment of the present invention.

FIG. 5 is a client-server architecture of one embodiment of the present invention. Web server 348 of server system 310 is connected via a communications network, e.g. the Internet 312, to client systems 320, 322, and 324. The server system 310 includes a backend server 340 connected to a scanner 342, a printer/fax 352 and a database 344, where database 344 stores electronic copies of the patient's medical records. The backend server 340 is connected to Web server 348. A client system 320 includes a personal computer (PC) 330 and a telephone 332, and printer (not shown). The PC 330 is connected to the Web server 348 via Internet 312. The telephone 332 is connected to a phone system interface 350 via public telephone system 314. Examples of the phone system interface 350 include a human interface, voice recognition unit (VRU), or automatic call system (e.g., for sending automated announcements to patients about keeping their records updated at specific time intervals.)

A patient's medical records, stored off-line in database 344, can be accessed by a client system, e.g., 320, through a scheduled "Session". A "session" is a time window in which the patient's medical information is available for access on Web server 348. The patient or the patient's authorized representative at, e.g., client system 320 uses telephone 332 to call phone system interface 350 to request a time window (e.g., start time and duration) to logon to Web server 348, and the patient receives a Session ID from the backend server 340. The Session ID instructs backend server 340 when, and for how long information is placed on-line for access. The client system 320 logs on to Web server 348 with the client's Login Name (or Member ID), password, and session ID at the given time. If the Session ID given by the client system 320 is the same as the session ID given by the backend server 340 to the patient via the phone system interface 350, then medical information on the patient, e.g., a portion or all of a patient's medical records, stored off-line in database 344 is transferred to a temporary storage location on Web server 348 by the backend server 340. If the session ID is incorrect or the patient logs on outside of the given time window, then no medical information on the patient is transferred to the Web server 348. When the patient logs off either explicitly or implicitly, e.g., by not entering information for a predetermined length of time or by exceeding the time window, the medical information on the patient is deleted from the temporary storage area on the Web server 348. 16

In one embodiment the phone system interface 350 is a call center whose operators use Web pages from the backend server to schedule a session for the patient. In another embodiment the phone system interface 350 is a phone server connected by a local network to the backend server 340, where only the requested time window and session ID for the patient is passed between the phone server and the backend server 340.

Figure 6:
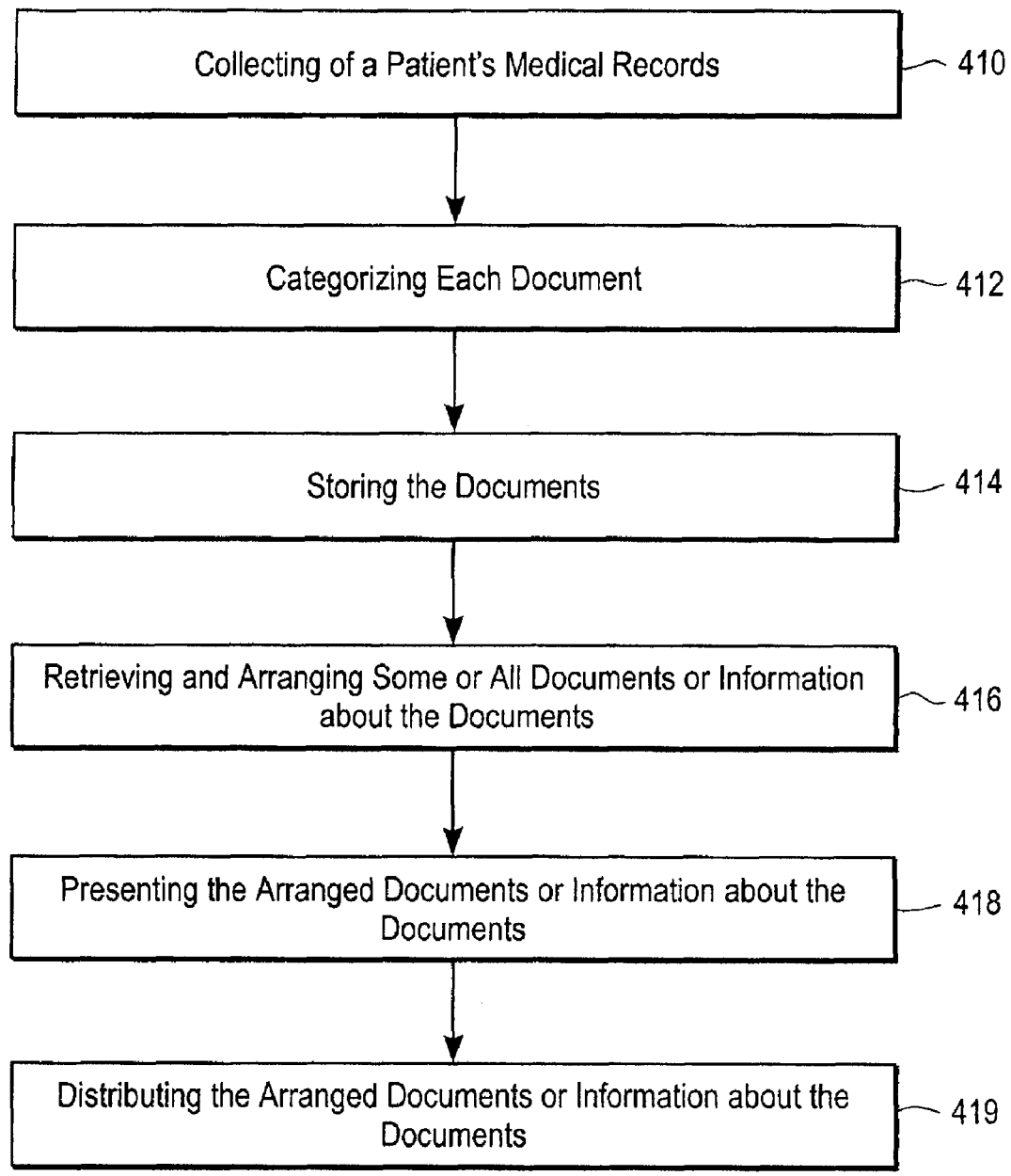
FIG. 6 is a flowchart for the process of managing a patient's medical records according to an embodiment of the present invention.

Record distribution can be done directly by a patient sending an email or fax from his client PC 330 or indirectly by calling a service entity by using the telephone system (332, 314, 350), which then retrieves relevant documents from backend server 340 for distribution via email, fax 352, CD-ROM (not shown), or hardcopy generated by printer 352 and then shipped off via traditional mail FIG. 6 is a flowchart for the process of managing a patient's medical records according to an embodiment the present invention. At step 410 the documents from a patient's medical records are collected from the patient's current and past healthcare providers. The documents may be collected in various forms to include electronic, paper-based, or film. For the documents that are paper-based, they are converted to electronic images by scanner 342. Each document in the patient's medical record is categorized (or classified) according to a predetermined categorization (or classification) system (step 412). In one embodiment all documents are converted into electronic format, except the medical images on film which are labeled with their categories, but not converted into electronic format. In an alternative embodiment, these medical images are also converted into electronic format. At step 414, the categorized electronic documents are stored in database 344. Upon request of a client system 320 to Web server 348 (with the appropriate session ID), backend server 340 retrieves and arranges some or all of the documents, using one or more of the categories, or retrieves information about the requested documents, e.g. number of documents in a given time period, from database 344 (step 416). The arranging of the documents, includes a sorting process using one or more of the categories, e.g., date of creation, and a predetermined sorting criteria, e.g., reverse chronological order. Next a filtering process is performed based on a predetermined filtering criterion, e.g., all of the sorted documents in the past year or all of the documents describing or listing medications. In another embodiment the filtering is done concurrently with the sorting. In yet another embodiment the filtering is done before the sorting. At step 418 the filtered arranged documents or information about the requested documents are sent via Web server 348 to be displayed on PC 330 at client system 320. The filtered arranged documents may also be emailed, faxed, stored in CD-ROM or printed and mailed on behalf of the patient (or for certain medical images retrieved from a film archive), either by page, section, or by the entire report, e.g., Combined Medical Records (CMR) report or Medical Summary (MS) report or the patient may print them for his own use using a printer (not shown) attached to a client system 330 (step 419).

Figure 7:
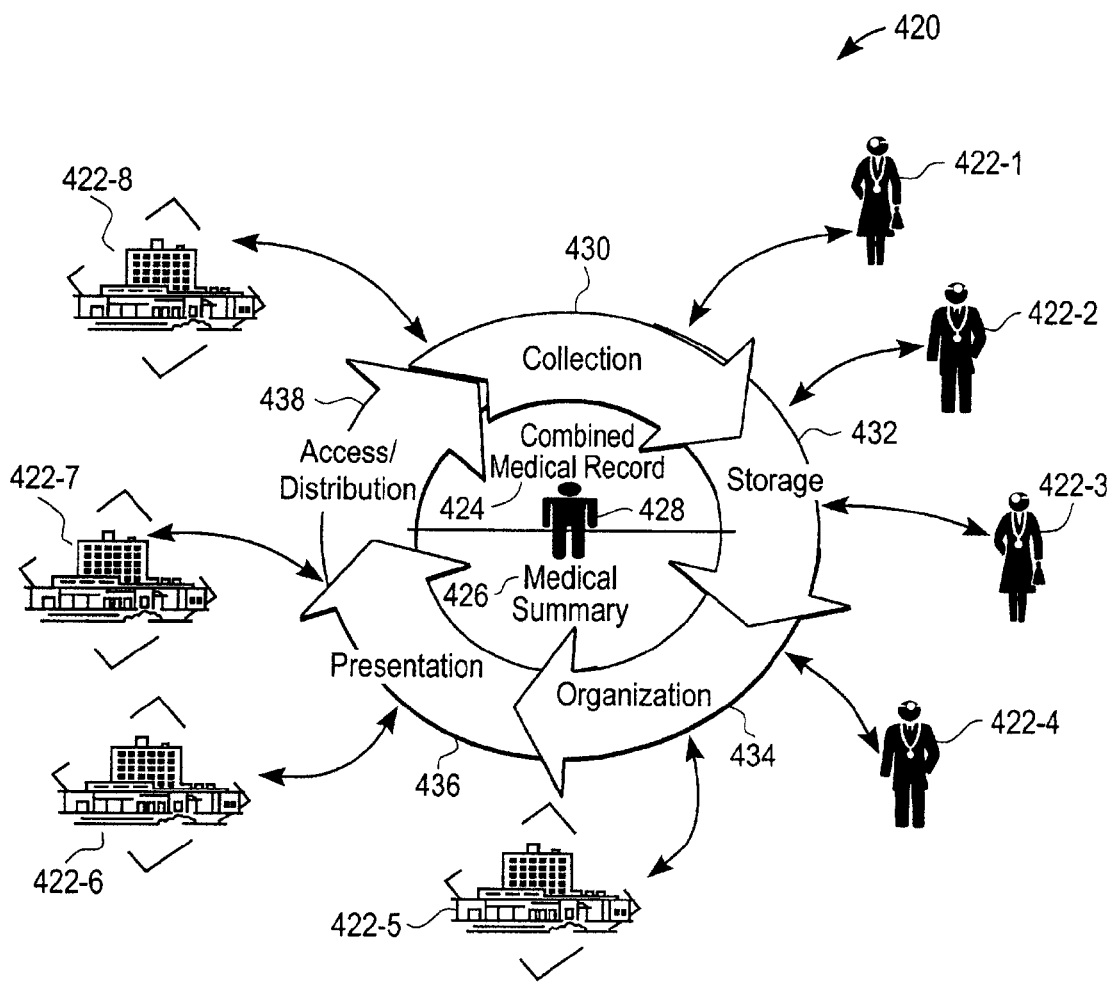
FIG. 7 shows the preferred process of managing a patient's medical records of another embodiment of the present invention.

FIG. 7 shows the preferred process of managing a patient's medical records of another embodiment of the present invention. The process is a cyclical process which receives a patient's medical records from a plurality of healthcare providers, e.g., 422-1 to 422-8 (both individuals 422-1 to 422-4 and organizations 422-5 to 422-8). The process then produces an output of either all or a portion of a Combined Medical Record report 424 or a Medical Summary report 426 or both that is an organized version of some or all of a patient's medical records. This output is then made available to the patient and to one or more of the plurality of healthcare providers, as authorized by the patient. The patient 428 is the center of this process and has the final say or control over which healthcare providers to request a copy of the patient's records, and therefore whose provider records are to be stored, and whom to authorize access for viewing and/or obtaining a copy. The process is performed preferably by a service provider, who acts on behalf of and with the permission of the patient 428. The process has a number of sub-processes: collection of initial records and of updates to these records 430, storage 432, organization 434, presentation 436 and online access and other forms of distribution 438.

At collection sub-process 430, a patient's initial medical records and any subsequent updates to these records are collected. The initial collection effort of a patient's medical records from the multiple healthcare providers consolidates a patient's medical data in one place, i.e., the patient directed central data repository, so that the patient's medical data can be reviewed on a comprehensive and as importantly, consolidated basis. A search engine using predetermined databases locates the whereabouts of a patient's past healthcare providers based on minimal information about provider's last name, city, and state. The healthcare provider is contacted in order to verify contact information, request record copies, and check record collection logistics. The patient is provided with periodic updates on the status of collecting his records. Each step of the collection process is automatically tracked.

Updates to the patient's initial medical records are collected to keep a patient's medical records current. Periodic "postcard reminders" or "email reminders" are set-up to remind the patient and his record providers to send in any new pages added to the patient's record since the previous collection. Using a database, the patient and record-provider are informed of the most recent type and date of documents collected. "Authorization stickers" to be pasted on lab tests or exam requests are mailed so that the tests and requests can be sent in for updating a patient's records.

At storage sub-process 432, the patient's medical records, including paper-based records along with a section for Patient Inputs, are stored electronically in a patient directed central data repository, e.g., database 344. A patient's medical records are stored permanently (or for as long as the patient wants) so that they are available for use in the future by the patient, his healthcare providers, his family members, and current and future offspring (legacy). The paper medical records are scanned into the computer, e.g., scanner 342 coupled to Backend server 340, enhanced, and orientated to give an upright presentation. Each scanned page is tagged with the patient's name, healthcare provider name, and file ID. In addition the patient inputs his medical information in order to give his perspective on his health and to offer one place for his healthcare providers to view all relevant patient-provided information. In an alternative embodiment, either the healthcare provider or a third party scanning service has previously converted the paper medical records into electronic images. As discussed before, each electronic image is tagged with the patient's name, record-provider name, file ID, and other useful categories.

At organization sub-process 434, the patient's medical records are organized across the multiple healthcare providers by pre-defined schema. This organization enables providers and patients to easily find and sort through pages of a patient's medical records. The categorization system is such that the same categories are used across the multiple healthcare providers. Hence, a standard set of categories are used for the documents from the multiple healthcare providers. The pages can be sorted by, section/categories, reverse chronological order, numerically by Document ID, alphabetically by name of the record-provider, name of the author or name of the medical specialization pertaining to the author. Every page is examined and assigned one or more categories of "page type." There are 30+ categories for describing the page type (or "medical category") of a particular page in a medical record file. These range from typical and commonly used (such as "Labs & Cultures", "EKGs", "Progress Notes"), to more detailed (multiple categories for Imaging, multiple categories for Hospital Notes, multiple categories for Labs & Cultures), then to even more refined classifications for narrowing the scope of the page search (such as difference between typed and un-typed notes; difference between "Inpatient" or "Outpatient" visits for doctor's or consultative notes.). In addition to these medical sub-categories ("Page Type"), there are several other indices used to categorize a page including: Patient Name, Member ID, Document ID, Author Name, Author Date, Author Specialization (to the extent that the author is a doctor), and Record-Provider Name.

At the presentation sub-process 436, some or all of a patient's medical record information is presented in reports. The presentation of the patient's medical information is consistent across the multiple providers in order to enable ease of use and understanding. The two main reports, i.e., the Combined Medical Records (CMR) and the Medical Summary (MS) reports, include most or all of the following presentation features: patient comment boxes, patient input forms, selected clinical pages (for the Medical Summary), patient-added pages (additional record pages to be extracted from patient's CMR and inserted into MS report for presentation), record indicators (availability factor and source factor calculated by algorithmic rules), document logs (by date, page type, and specialization), and visual time lines (timeline of documents and timeline of progress notes).

At access/distribution sub-process 438, on-line access by patient himself or by patient-authorized third party to a patient's medical records via an Internet browser is also provided. Online access enables access and availability of a patient's medical records when they are needed, and anywhere where there is Internet connection. For standard (non-emergency) access, the security and access protocols are based on an approach from a risk management standpoint, which limits the amount and length of time a patient's data can be accessed via the Internet. The access protocol limits exposure of data to unauthorized access by controlling the amount of data made available and when the data is accessible via the Internet. For emergency access, the scope of content in the patient's medical records is limited for unknown (undesignated) 3rd party healthcare providers.

Further at access/distribution sub-process 438, a patient distributes some or all of his medical records to third parties where needed. Distribution requires a patient's authorization on a "Send To" form before distribution can begin. The Medical Summary and/or Combined Medical Records report can be distributed in several formats, including: individual pages, sections, or the entire report copy. Patients can make distribution requests from their personal pages on the web server or by telephone, fax, email, or mail. Distribution can be made by, but is not restricted to, fax, email, CD-ROM, paper copy, or a bound copy.

Examining FIG. 7 in more detail, collection sub-process 430 requires the identity and address of the healthcare provider, before a patient's medical records can be collected from that healthcare provider. Once the identity and address of the healthcare provider is known, server system 310 automatically generates a letter for the patient's signature to request a copy of the patient's medical records from the physician or health-care provider organization.

Figure 8:
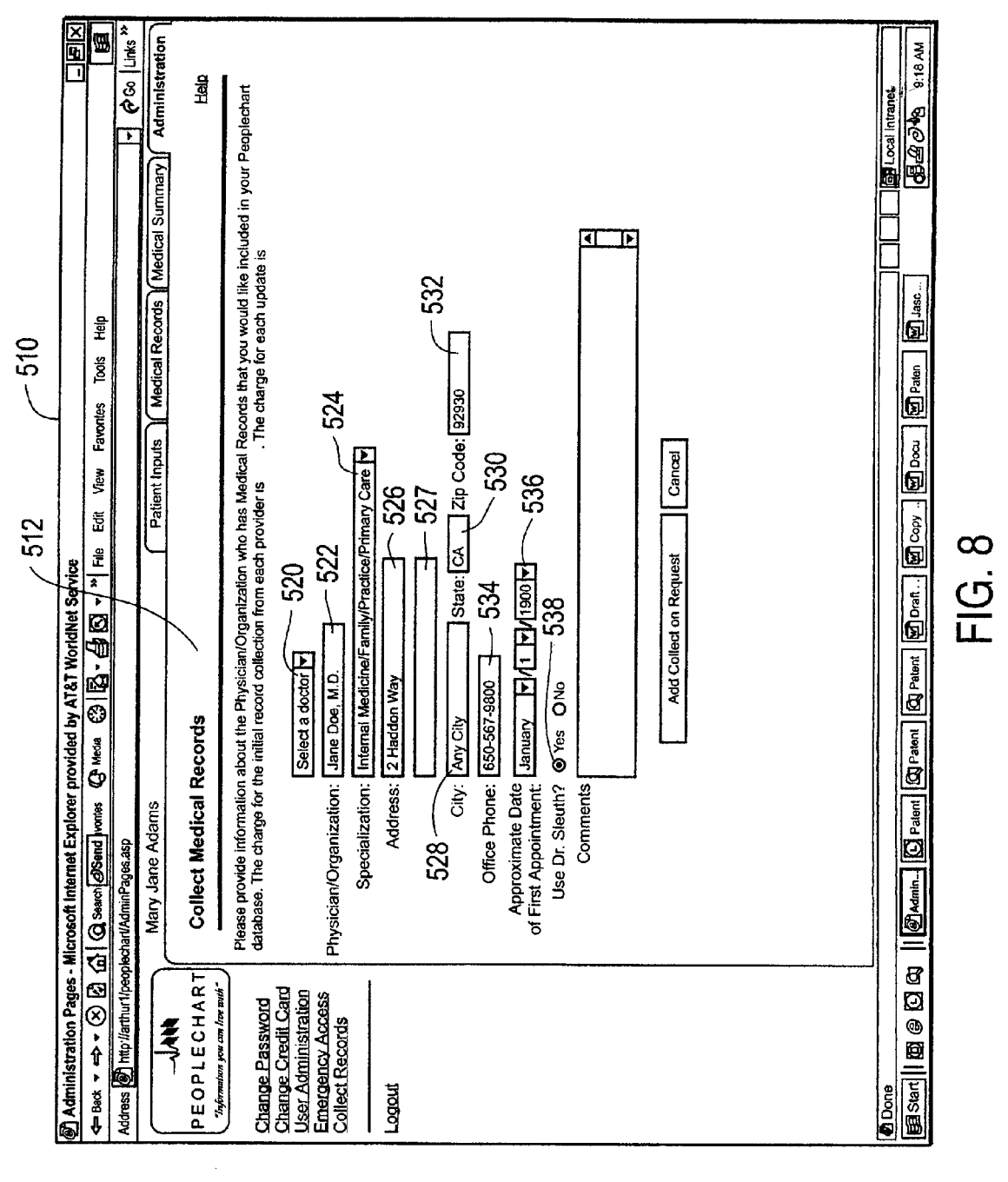

FIG. 8 is an example of a user interface for a healthcare provider search engine of an embodiment of the present invention. In the preferred embodiment, this search engine is used by the service provider in the collection sub-process to locate the patient's healthcare provider. In an alternative embodiment, the search engine is a stand-alone that can be used to locate any healthcare provider. The user interface 512 executes on a Web browser 510, that is displayed on client system PC 330. The user interface 512 allows the patient to fill in partial information about a current or past healthcare provider, for example, the patient could provide some minimum information such as a doctor's last name (or organization name), city, state, and specialty, and the search engine, executing on Web server 348, searches several databases to locate the rest of the doctor's (or organization's) location information. User interface 512 includes a selection 520 to choose the type of healthcare provider, e.g., a doctor, an input area 522 to enter the name of the physician or health-care organization, e.g., Jane Doe, M.D., and a selection 524 to choose the specialization of the physician or organization. User interface 512 further includes several address input areas, 526, 527, 528, 530, and 532 to enter the current address of the doctor or health-care organization. Typically, the required address entries are for the city 528, e.g., Any City, and state 530, e.g., CA, or alternately, the zip code 532, e.g., 92930. User interface 512 further includes entry areas for the office phone 534 and for the approximate date of the first appointment 536. There is a selection button 538, that when selected, automatically searches a plurality of predetermined databases to fill in the rest of the location information, e.g., address 526 and 527 of the physician or organization. Table 1 below gives examples of web sites that the search engine searches to find the missing location information. In an alternative embodiment the search of the Website in Table 1 is done manually. In another embodiment the research for locating the provider is done using non-Web resources.

TABLE 1 http://www.docboard.org/
http://www.ama-assn.org/aps/amahg.htm
http://www.chiropractor-dir-ectory.com/
http://www.theinternetdirectories.com/thehealthcaredir-ectory/
http://www.sermed.com/hospital.htm
http://www.nationalhospital.com/index.html
http://www.hospitalselect.com/curb_db/owa/sp_hospselect.main
http://neuro-www2.mgh.harvard.edu/hospitalwebusa.html
http://www.thephysiciansdirectory.com/
http://www.thedentistdirec-tory.com/

After contact information in FIG. 8 is either filled in by the user or by the search system, a request for the patient's medical records from the Physician/Organization 522 is created. Next, a Collection Request ID is assigned to the request along with inputs for specific record fields identified by the Collection Request ID, the Member's (i.e., patient's) ID, the information from FIG. 8, the date of the request and the status of the request is inserted into the CollectRecords table of the database 344.

The collection process can be in one of the several states, including: 1. Record collection request received, waiting for authorization form from member (i.e., patient); 2. Authorization form received records requested from provider; 3. Records not received from provider, second request sent; 4. No response to second record request, third request sent; 5. No response to third record request, review options with member; 6. Records received, waiting to be processed; and 7. Records processed into database. The current collection status is updated by personnel of the central data repository service via a window similar to window 510, but with an extra pull-down menu that allows one of the above seven status states to be selected or updated.

Figure 9:
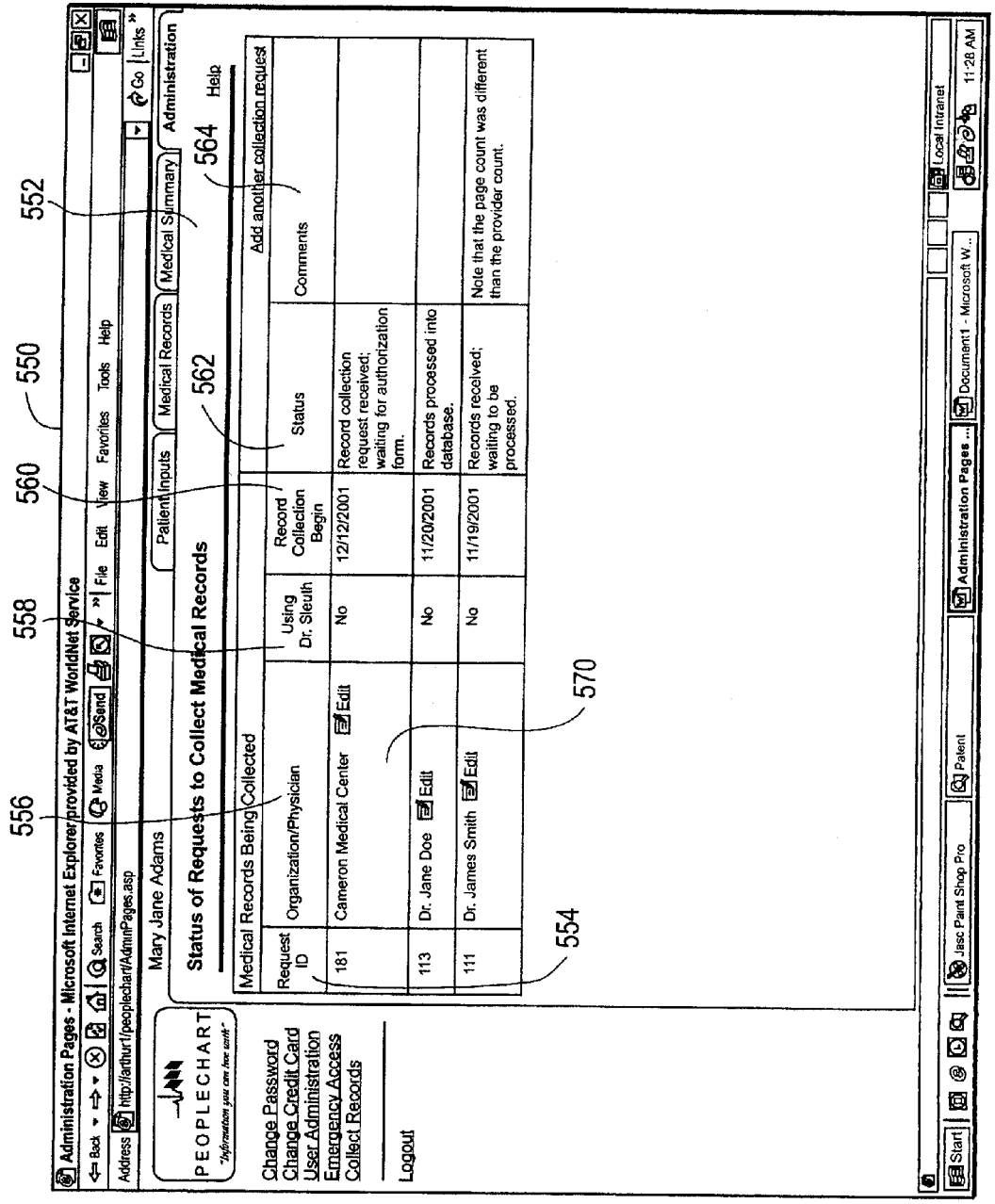
FIG. 9 is an example of a user interface showing the collection status of a patient's medical records.

FIG. 9 is an example of a user interface showing the collection status of a patient's medical records. The display 550 includes the window 552 (Member Administration) that has the record status. In column 554 is the collection request ID for each request. In column 556 is the name of the organization or physician to whom the record request is sent, for example, "Cameron Medical Center" in box 570. Also the "Edit" link in box 570 brings up a window for "Cameron Medical Center" similar to FIG. 8, and allows the information in FIG. 8 to be changed. Column 558 displays whether or not the search engine was used to fill in missing contact information in FIG. 8. Col. 560 gives the date the record collection began. Column 562 gives which of the seven states, listed above, the present collection status is in. Column 564 has comments related to collection of the medical record.

Once the patient's medical records are received, every document is examined and categorized (organization sub-process 434). For paper based medical records, each page is scanned via scanner 342 into an electronic image, stored in TIFF format, and then converted into PDF format, once categorization is done. Each electronic image is examined and categorized. Among the categories assigned is a page category that has a plurality of medical sub-categories. These medical sub-categories include, for example, documents on typical medical results and notes, such as a "Labs & Cultures" sub-category, a "Consultations" sub-category, a "EKGs" sub-category, and a doctor's "Progress Notes" sub-category. Some pages could have multiple medical sub-categories (cross-referenced). The "Immunizations" sub-category, for example, has documents that are also found in the "Progress Notes" sub-category and in "Physical Exams" sub-category. In an alternative embodiment, some or all of the paper-based records have been previously scanned at the healthcare provider and these scanned image files are examined and categorized, i.e., no scanning is needed by the server system 310.

Figure 10A:
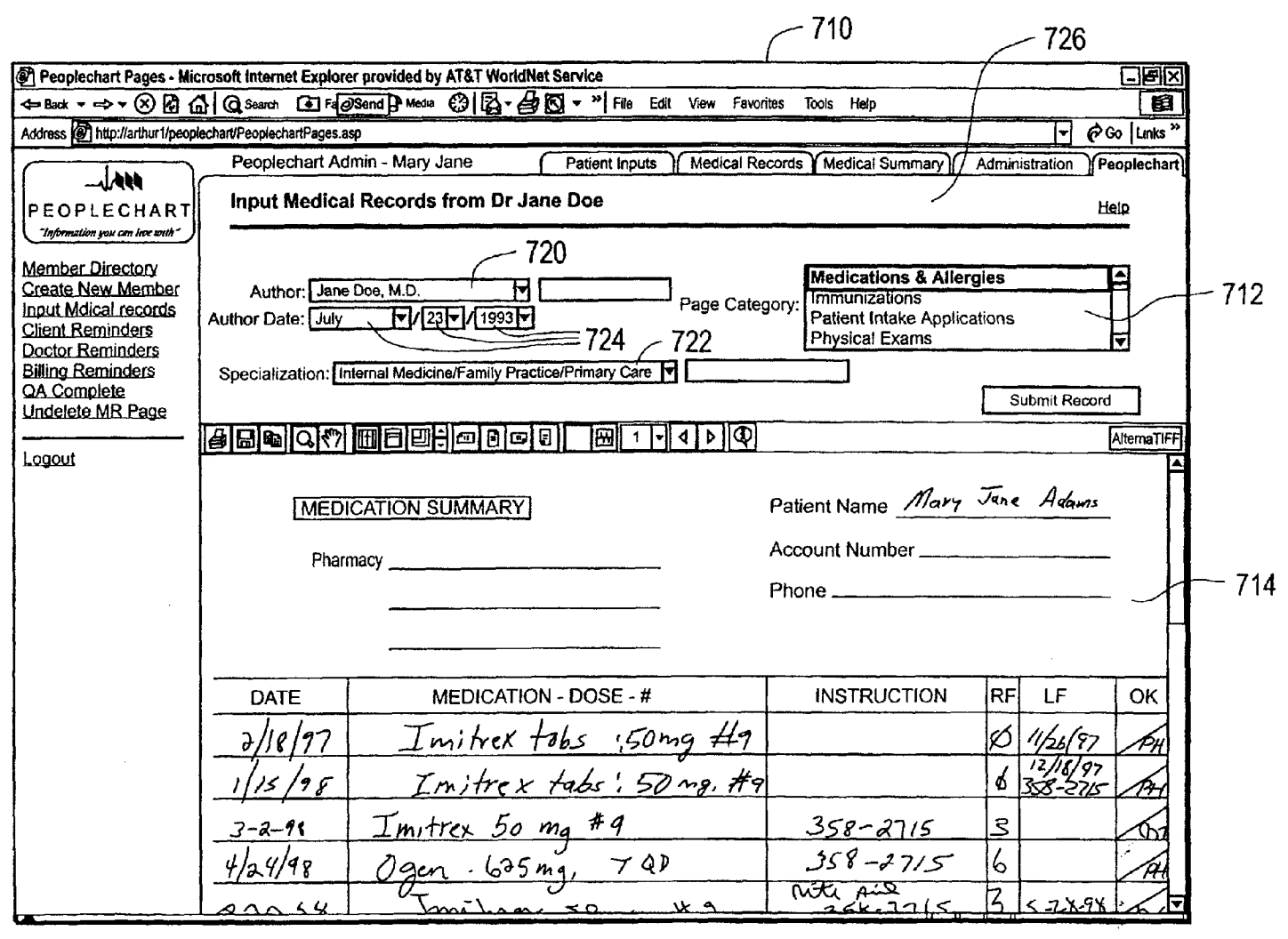

FIG. 10A is an example of a user interface for categorizing a scanned page of an embodiment of the present invention. The scanned page shown in window 714 is of a medication summary of patient Mary Jane Adams. Window 712 is used to assign categories to the scanned page in window 714. Window 712 includes an entry area 720 for the author of the scanned page, a menu 722 to select the specialty of the author given in entry area 720, menus 724 to enter the date the author generated the paper-based page, and a menu 726 to give the page type, i.e., medical sub-category as listed in FIG. 15, and cross-indexed (given an alternative page type), where it makes sense.

When the information in FIG. 10A is submitted to the Backend server 340, a Document ID is assigned to the scanned page and the Document ID, the information from FIG. 9, the Collection Request ID, the Member's ID, the Record-Provider's Name, and the date the record was entered is inserted as a record into the DocumentLog table of the database 344. The scanned page is formatted into a PDF format file with a header and a footer having labels of one or more categories. The formatted file is stored as an electronic image file (for example FIG. 11) with the Document ID as the filename and a .pdf extension.

Figure 10B:
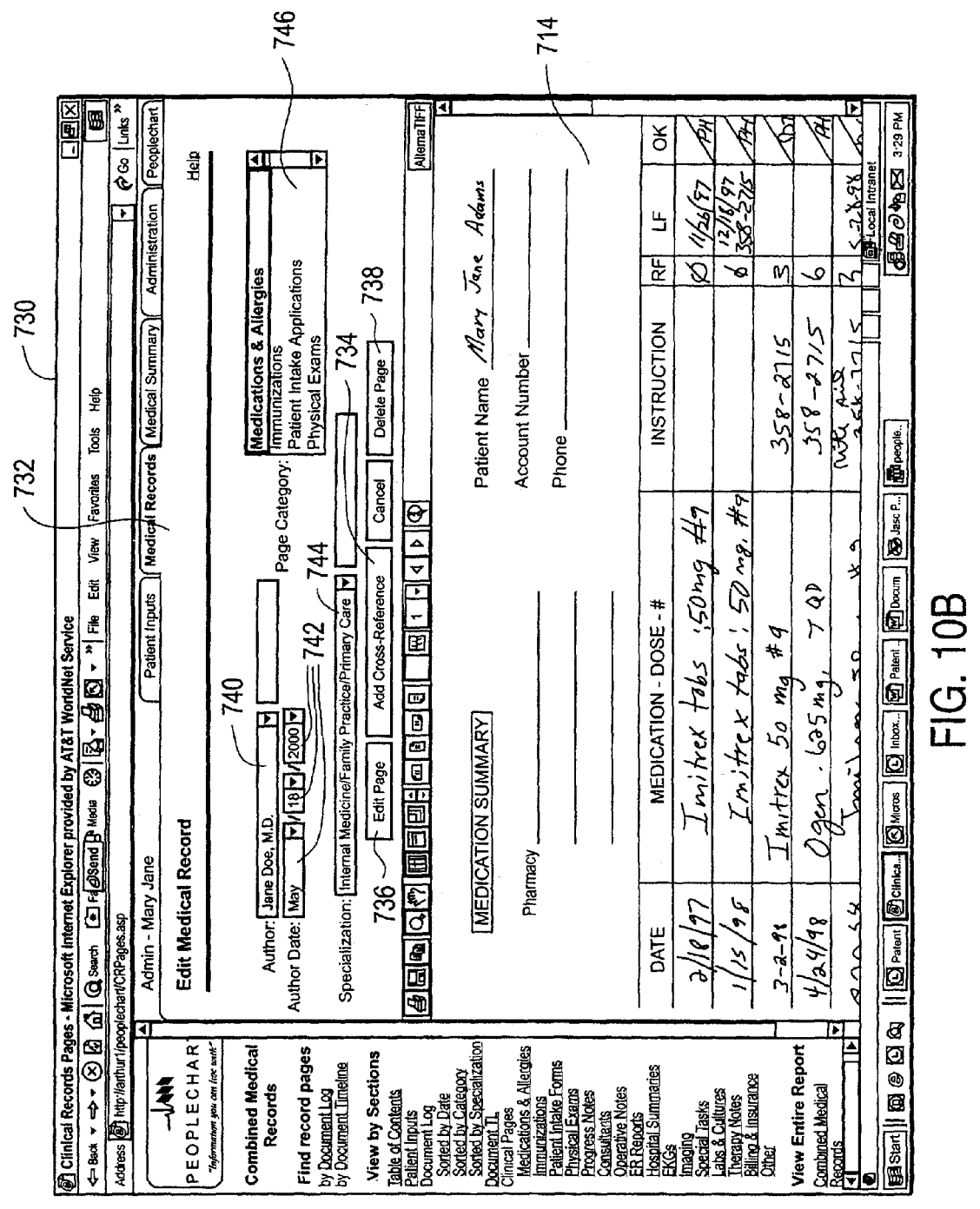

FIG. 10B is an example of a user interface for a system of cross-indexing, i.e., adding an additional category to an already categorized page or making edits to the categorization of a scanned page. Selection 734 allows other medical sub-categories as given in FIG. 15 to be added as classifying categories for the page 714, i.e., cross-indexing. These additional medical sub-categories can be used to search and sort the page 714. There is also the choice 736 to make edits to the author 740, date 742, or specialization 744 of an already categorized page 714. Also selection 738 allows deleting a page that has been duplicated for cross-indexing purposes.

FIG. 11 shows an example of an electronic image 810 with the categories added to the header 814 and footer 816 of scanned page 714 of FIG. 10A. The categories shown in this example in the header 814, include: the document identifier, "Document ID: 455" 820, the page type (medical subcategory), "Medication and Allergies" 822, the patient's name, "Mary Jane Adams" 824, and the patient's member identifier, "MemberID 532" 826. In the footer 816 the categories shown include: the author of this page, "Author: Jane Doe, M.D." 830, the doctor's specialization, "Specialization: Internal Medicine/Family Practice/Primary Care" 832, the date the author created the document, "Author Date: May 18, 2000" 834, and the name and number of the service provider, "Peoplechart (415)-362-8800". In addition any hardcopy of any electronic image is also labeled with these descriptive fields in the header and footer. Hence pages can be easily traced back to a particular file or section, date, or record provider name, and re-ordered when they become disorganized.

In one embodiment the categories for the header that appear on each page include: Document ID, Patient Name, Page type(s), and Patient's Member ID. And the categories for the footer of each page include Author of the page, Specialization of the Author, if relevant, Date in which page content was created, and optionally, the service provider's phone number. A category that does not but could appear on the example page is the name of the record-provider who provided the records. In most cases, this can be an important organizational tool for those patients who see multiple healthcare providers and want to find the pages that belong to a particular healthcare provider. In other embodiments some of the information in the header may be absent or in the footer and some of information in the footer may be absent or in the header. In an alternative embodiment, other categories may be added to the header or footer, such as patient aliases, maiden name, patient's date of birth, healthcare provider, or additional categories apparent to one with ordinary skill in the arts.

Figure 12:
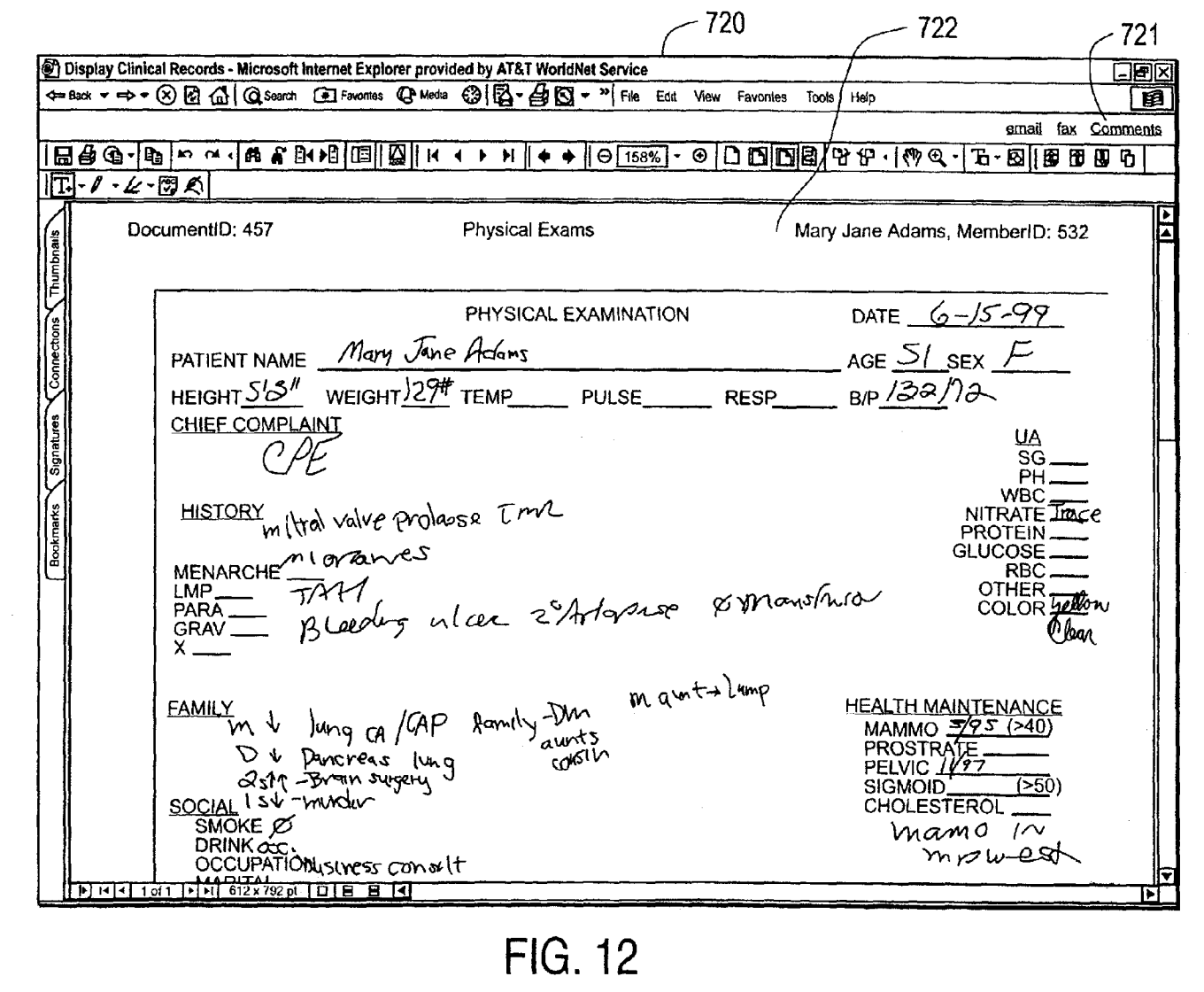
Figure 13:
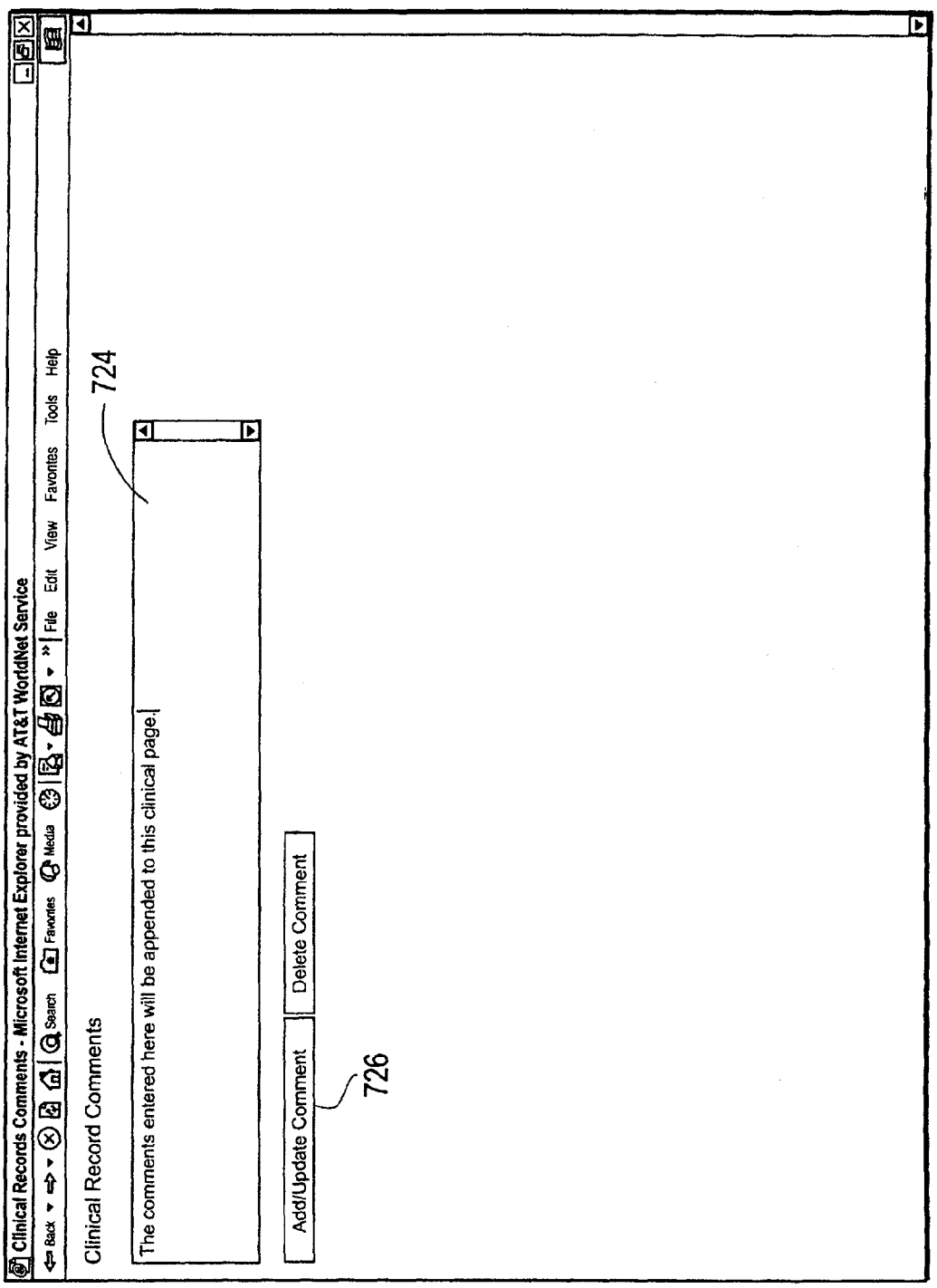
FIG. 13 shows an example of a comment box in which the patient can enter his own comments related to the physical exam summary page of FIG. 12.

A patient and/or the patient's doctor(s) can add comments to the electronic copy of their medical records by launching a comments dialog box. The comments then become an integral part of the medical record, i.e., the comments are electronically linked to the medical record. This provides the patient with a valuable tool to update, correct and add to the informational contents of the medical record. FIG. 12 is an example of a window 720 of a physical exam page 722 of a patient's medical records. The comments link 721 in FIG. 12 is used to launch the comments dialog box. FIG. 13 shows an example of a comment box 724 in which the patient can enter his own comments related to the physical exam summary page 722 of FIG. 12. In this example the patient types "the comments entered here will be appended to this clinical page". When the "Add/Update Comment" button 726 is clicked the comment is appended (or linked) to the medication summary page 722.

Figure 14:
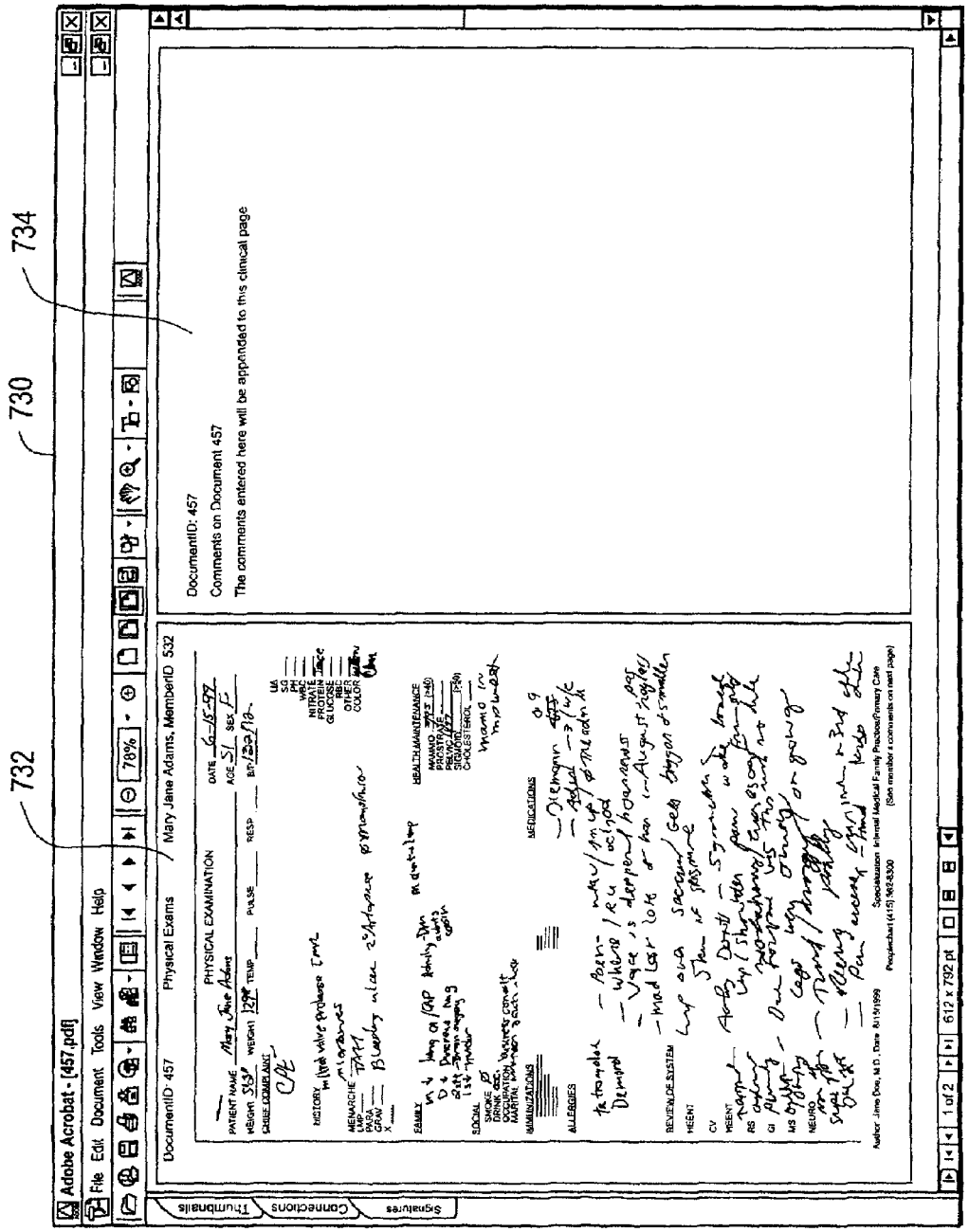
FIG. 14 is an example of a document appended with patient's comments.

FIG. 14 is an example of a record page document with a patient's comments appended to it. Page 732 is the physical exam page 722 of FIG. 12. The comment page 734, which is attached or linked to the physical exam page 722, has the comments typed in comment box 724 of FIG. 13.

FIG. 15 lists the medical sub-categories describing page type category of an embodiment of the present invention. In this example there are 35 medical sub-categories associated with the page type category as shown by "Index ID", column 912. The table 910 in FIG. 15 includes a column 920 having a description of each medical sub-category, and a column 922 for the code used for each sub-category. Also included in table 910 is a column 914 showing the sub-sections in the "Clinical Pages" section of the Combined Medical Records (CMR) report; a column 916 showing the section numbers for the document timeline graph; and a column 918 showing the sub-section numbers of the "Selected Clinical Pages" section for the Medical Summary (MS) report.

Some of the medical sub-categories in FIG. 15 have been broken down from a more general sub-category in order to help a doctor find information quickly, including 6 sub-categories for Imaging, 5 different sub-categories of Hospital Notes, and 3 different sub-categories of Labs & Cultures. There are also sub-categories for helping patients and doctors to quickly select or differentiate the pages they want within those categories, such as Typed versus Untyped (handwritten). There are also 5 categories of "Other" to address and separate duplicate pages, irrelevant pages such as those concerning a different patient, title pages from healthcare provider files, and administration type pages. Thus all documents of a patient's medical history are categorized with at least one medical sub-category given in FIG. 15. The categories given in FIG. 15 are not to be interpreted as limiting, but are a preferred embodiment of the present invention. Other embodiments may have different categories or the same or a different number of categories. For example, The "Medications and Allergies" sub-category could be further divided into traditional and non-traditional medications.

Once the categorized documents are stored in database 344, these categorized documents can be sorted and/or searched. Pages can be found in a selected category or sub-category by using "Search By" category fields displayed on a client system, e.g., client's personal computer 330. Moreover, pages can be re-categorized into different categories at the request of the patient. The categorized documents can also be sorted into a tabbed collection of documents and presented as a report, e.g., the Combined Medical Records (CMR) or Medical Summary (MS) report, as described with tab names displayed in the order of prioritization as shown on 914 and 918 (FIG. 15), respectively. These reports are either presented on the client system, e.g. 320, using a Web browser connected to Web server 348, emailed as an attachment, faxed, saved on a CD-ROM or printed, or both.

The Combined Medical Records report is an organized and comprehensive portfolio of a patient's medical history. The CMR includes both clinical record pages collected and compiled from a patient's current and past healthcare providers and a section called Patient Inputs, which provides an opportunity for patients to add their perspective and assessment of their health history, condition, and objectives. The CMR further includes organizational tools such as document logs, providing a page-by-page inventory of the medical records in the patient's files and a time line of activities represented by documents collected over the course of a patient's health history. An example of a CMR outline by section and sub-section is given in Table 2 below.

TABLE 2

| SECTION | SUB-SECTION |
|---|---|
| A. Table of Contents | |
| B. Patient Inputs | |
| C. Document Logs | |
| | 1. By Date |
| | 2. By Medical Category |
| | 3. By Specialty |
| D. Document Timeline | |
| E. Clinical Pages | |
| | 1. Medications & Allergies |
| | 2. Immunizations |
| | 3. Patient Intake |
| | 4. Physical Exams |
| | 5. Progress Notes |
| | 6. Consultations |
| | 7. Operative Notes |
| | 8. ER Reports |
| | 9. Hospital Summaries |
| | 10. EKGs |
| | 11. Imaging Reports |
| | 12. Special Tests |
| | 13. Labs & Cultures |
| | 14. Therapy Notes |
| | 15. Billing & Insurance |
| | 16. Other |

A patient may designate any document in his medical records as "Private". These "Private" documents are only viewable by the patient and are not included in the CMR or MS reports. If the patient wants to provide "Private" documents to another party, this can be done on a per document basis.

Figure 17:
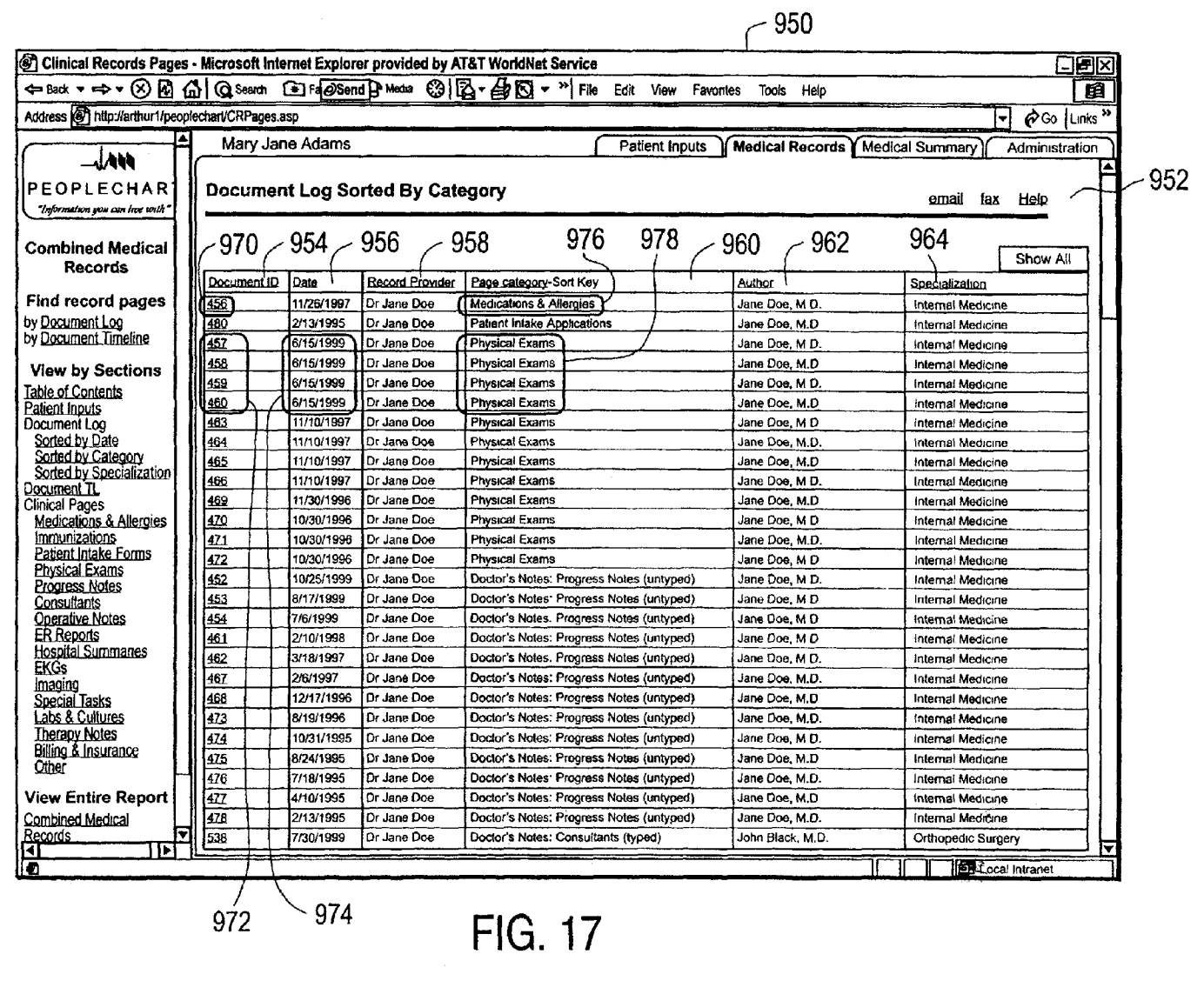
Figure 18:
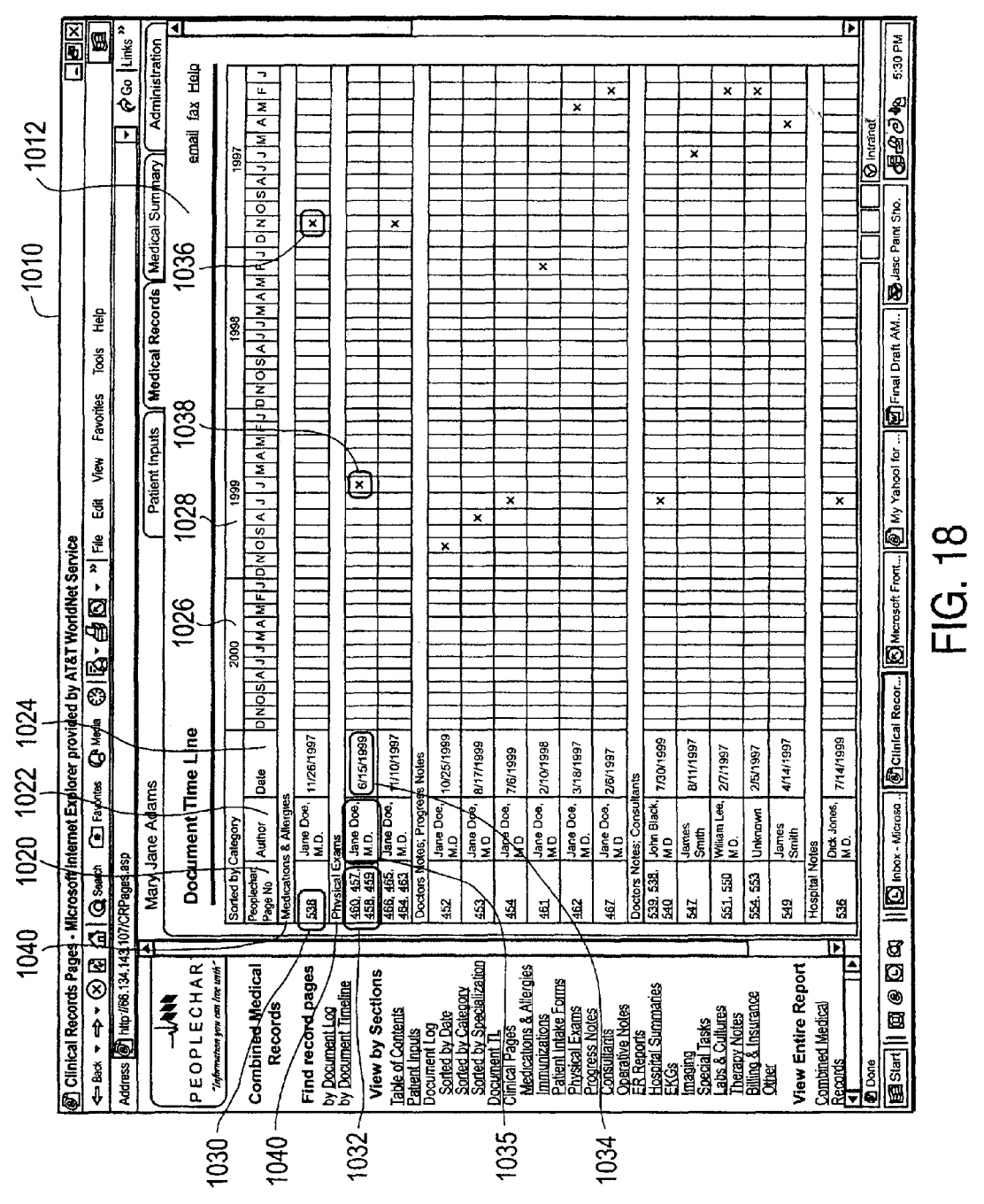

FIG. 16 is an example of a user interface 930 allowing the designating of some of a patient's medical records as "Private". FIG. 16 has information in its columns similar to FIG. 17, except there is a "Private" column 932, that allows a patient to select which documents in column 954 are to be designated "Private". After the patient checks the checkboxes, e.g., checkbox 934, of the private documents, he clicks the button "Hide Private" 936 to complete the hiding process, i.e., only the patient can view the private documents. Hiding Document 455 (checkbox 934) means that the information relating to Document 455 will not appear in the document logs, timelines, or reports as illustrated in FIG. 17 and FIG. 18.

Both the CMR and MS reports have record indicators to inform the doctor whether some of the patient's medical records are missing from the report, i.e., marked "Private" in the database. Another record indicator that informs the doctor whether the clinical pages were provided by another healthcare provider or by the patient. These indicators assist the doctors in determining the reliability of the medical records.

"Availability" factors are calculated and displayed for each sub-section of the clinical page section of the CMR and for the whole report. These factors are also applicable to each sub-section of the selected clinical pages of the MS. The availability factor is the ratio of the number of pages presented in the report to the total number of pages collected, by section and by entire report. This indicates to the physician whether some pages have been classified as Private and are not available for viewing. For example, an availability factor of 75% on a subsection of four documents means for example, that 3 out of the 4 documents in the subsection are included in the sub-section, while one document has been excluded from the presentation or marked as "Private."

"Source" factors help measure the classification of the source, individual or organization who sent in the records, for each sub-section of the clinical pages in the CMR and for the whole report, i.e., those records provided or sent in by a patient versus those records sent in or provided by provider. Since many physicians are concerned that they have a complete set of records, they assess the credibility of these records by the source-sender of the records, i.e., whether the records have been obtained directly from a healthcare provider or indirectly from the patient. This information is provided as a ratio of the number of clinical pages in a medical sub-category obtained directly from healthcare providers to the total number of pages in this medical sub-category. A source factor of 90% in a subcategory having ten pages would indicate that nine pages came directly to the data repository service from the healthcare provider, and one page came from the patient.

After the "Table of Contents" section, the next section in the CMR is the "Patient Input" section. The patient input section allows a patient to share his perspective of his health with his doctor. This section includes: a patient's assessment of his health history, current health condition, and objectives; clinical information that the patient himself fills in order to supplement his medical records, such as medications, immunizations, and allergic reactions; and personal and medical contact information, health insurance, and administrative information. The patient input section includes two major parts completed by the patient. Part I provides the patient's personal and medical information, description of health statistics, family history, and assessment of his health conditions. Part II provides medical and personal contacts for times of medical emergencies and other relevant administrative information.

The Part I, Health Assessment, is further divided into: personal information, current health concerns, health history, allergies & reactions, medications, doctors be aware, general health & background (including immunizations), hospitalization history, family health history, alternative/complementary medicine, and health objectives & experience. Part II, Personal Contacts and Administrative Information, is further divided into: doctor contact information, emergency contact information, employment information, and health insurance.

The third section in the CMR is the "Document Logs" section. Document logs provide an inventory listing of every page contained in a patient's collected medical records. This list can help the patient and her doctor spot a specific clinical page or review the amount, type, and timing of clinical documents available in the patient's files. Pages may be sorted by sub-categories, for example: 1) Document ID#, 2) Document date, 3) Record-provider name, 4) Page type by medical sub-category, 5) Author of the document and 6) specialization of the author. In one embodiment, the CMR documents are sorted by the document date, by medical subcategory, and by doctor specialization to produce three different logs.

A document log sorted by date, provides an inventory of pages in a patient's compiled records, presented in reversed chronological order based on the date shown for creation of the page content. When a document cannot be dated based on information from the page, a default date is chosen that places the document at the end of the log. With default dates, the patient is advised to review and provide a date if known or available. When a document has multiple dates listed on the page, such as pages found in Progress Notes or Medication Refill Logs, the most recent date is chosen. However, due to the fact that there are usually multiple dates for Progress Notes, pages of this type are shown separately in its own Timeline table.

A Document log sorted by medical category provides an inventory of pages in a patient's compiled records, organized by sections made up of commonly used medical sub-categories such as medications & allergies; hospital summaries; labs & cultures; etc. (see FIG. 15). Within each sub-category, pages are sorted in reversed chronological order. When a document cannot be placed in a specific medical sub-category, it is placed in a sub-category labeled "Other: Unclassified" and placed at the end of the log.

A document log sorted by specialization organizes the pages based on the specialty of the doctor or provider who wrote or created each page. This log provides an inventory of pages in a patient's compiled records, organized by name of the specialty of the physician(s) who authored the pages. The ability to sort charts by specialty helps patients bring information that is most relevant to their doctors, especially when they see a specialist about a particular condition. Pages authored by a location or an organization (such as a health clinic or laboratory) can be difficult to classify into specialties and are left for the patients or their doctors to categorize by relevant specialty. A document which cannot be categorized by specialty of author is included in a category labeled, "Unknown Specialty" and placed at the end of the log.

While the CMR provides three logs, other document logs based on the other categories can be generated and displayed. FIG. 17 is an example of a document log sorted by medical sub-category of an embodiment of the present invention. The window 952 includes the document log sorted by the medical sub-categories of FIG. 15. Column 954 gives the document ID for each document. Cell 970 has document ID 456, which is a link to the document image, e.g., the scanned image of the page (while document ID 455 (as selected by checkbox 934) is hidden from view as a result of having clicked on "Hide Private" button as described on FIG. 16). When "456" is selected a separate window (not shown) opens with the document's image. The four cells 972 have document IDs 457, 458, 459, and 460, which all have the same date 974, i.e., "Jun. 15, 1999" and the same page type "Physical Exams" 978. The window 952 further includes, column 956 which has the date the document was created, column 958 has the healthcare provider that provided the document, column 960, "Page Category" and the primary "Sort Key" in this example, has the medical sub-category from FIG. 15, column 962 has the name of the doctor who created the document, and column 964 has the specialization of the doctor in column 962.

The fourth section in the CMR is the "Document Timeline" section. A timeline shows the pattern of events in the course of a patient's medical history by tracking the number of documents collected over time by sections made up of commonly used medical sub-categories (see FIG. 15) such as medications & allergies; physical exams, hospital summaries; labs & cultures; EKGs; imaging reports; and consultations with doctors, etc. Within each medical sub-category of the timeline, each mark on the timeline is identified by its unique combination of creation date and creator name (author). For each sub-category, each individual mark on the timeline can represent one or more pages that have the same date and author. Said another way, document that is made up of multiple pages (such as lab results) share only one mark on the timeline. The patient and doctor can visually gauge the type and frequency of activities performed by reviewing the number of "X's" that document(s) collected over the course of the patient's medical history by medical sub-category. Both patient's and doctor's comments about the timeline are provided at the end of section.

Figure 19:
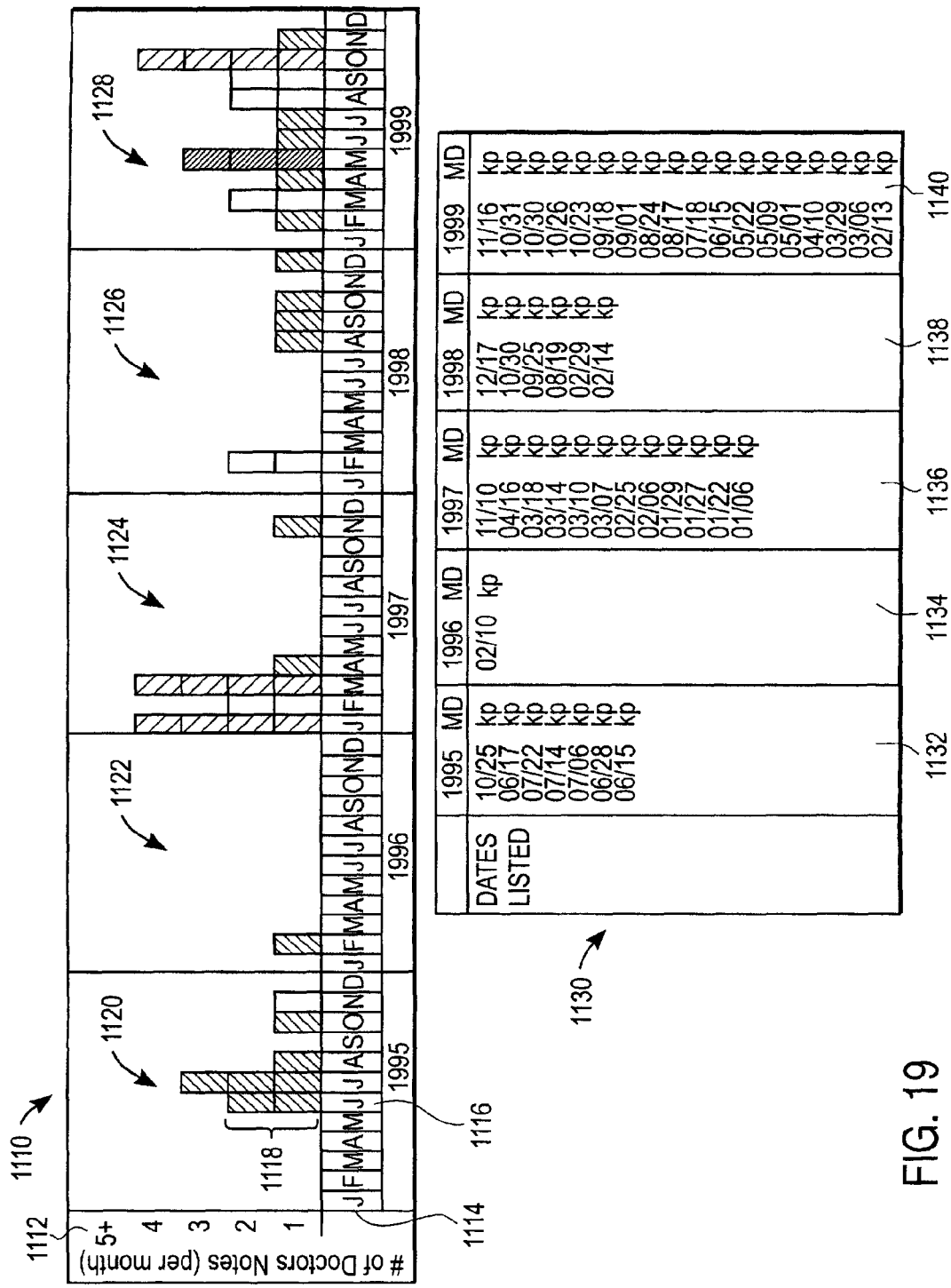
FIG. 19 is an example of a timeline of the number of a doctor's progress note of an embodiment of the present invention.

FIG. 18 is an example of a document timeline for FIG. 17 of an embodiment of the present invention. Window 1012 includes a column 1020 having the Document ID, column 1022 having the author of the document, column 1024 having the date the document was created, and a time line divided by months, e.g., the 12 months for year 2000 1026 and the 12 months for year 1999. In addition, the window 1012 shows several sections, e.g., a "Medication & Allergies" section 1040, that includes document ID 456 in cell 1030 (while document ID 455 (as selected by checkbox 934) is hidden from view as a result of having clicked the "Hide Private" button 936 as described in FIG. 16), and a "Physical Exams" section 1040, that includes document IDs 460, 457, 458, 459 in cell 1032, since they all have the same date "Jun. 15, 1999" 1034 and same author "Jane Doe, M.D." 1035, these documents get one mark only, 1038. For document ID 456 (cell 1030), there is mark 1036 on the timeline. For document IDs 460, 457, 458, 459 (cell 1032) there is mark 1038 on the timeline. FIG. 19 is an example of a timeline of the number of a doctor's progress note of an embodiment of the present invention. The timeline 1110 has the number of progress notes on the y-axis 1112 and the time, e.g., month, on the x-axis 1114. For example, in June 1116 there were two progress notes written 1118. The timeline 1110 is segmented by years, 1120, 1122, 1124, 1126, and 1128. A table 1130 lists actual dates in the month the progress notes were written. Table 1130 is also segmented by year 1132, 1134, 1136, 1138, and 1140 to correspond to years 1120, 1122, 1124, 1126, and 1128 of timeline 1110, respectively. The progress notes may be color coded to represent the different providers who authored the notes.

The fifth section in the CMR is the "Clinical Pages" section. Medical record documents collected from a patient's past and present doctors are arranged into commonly used medical sub-categories (FIG. 15), and sorted by date in reverse chronological order. The sub-sections of the CMR for the "Clinical Pages" section are listed in Table 2 above.

Sub-section 1. The Medications & Allergies sub-section of the "Clinical Pages" section includes refill logs, medication notes, any pages in progress notes section referencing medications, and any pages in physical exams section referencing medications. This sub-section can be cross-referenced to the patient input sub-sections for allergies and reactions and medications. In one embodiment the cross-reference is done manually by the patient's doctor or medical records technician. In an alternative embodiment, there is a "cross-referenced" button on the display window so that a page can appear in multiple sub-sections of the CMR and Medical Summary Report. The cross referencing is done by the service provider. In an alternative embodiment the cross referencing may be done by the patient and/or healthcare provider.

Sub-section 2. The Immunizations sub-section includes documentation of immunization given to the patient. Pages may be cross-referenced to the progress notes, physical exams sub-sections, and to the general health & background of the patient input section.

Sub-section 3. The Patient Intake Applications sub-section includes an application usually filled out by patient during a first visit with a doctor.

Sub-section 4. The Physical Exams sub-section includes notes (typed or handwritten) related to patient during a physical examination.

Sub-section 5. The Progress Notes sub-section includes notes from a first visit and any subsequent outpatient visits with the patient's doctors.

Sub-section 6. The Consultations sub-section includes physician consultation notes from any outpatient setting.

Sub-section 7. The Operative Notes sub-section includes notes related to both inpatient and outpatient procedures, surgeries, and operations, performed in clinics or hospitals.

Sub-section 8. The ER Reports sub-section includes notes from visits to emergency rooms of hospitals or clinics.

Sub-section 9. The Hospital Summaries sub-section includes in-patient notes and consultations taken during patient's hospitalization, such as Admitting History & Physical, Discharge Summary, Consultations (Inpatient), Progress Notes (Inpatient), and any other hospital notes. Surgical, operative and procedure reports and notes, which are found in Operative Notes sub-section are excluded. Also any outpatient visits to clinics or hospitals, which are found in Consultations, Progress Notes, or Physical Exams sub-sections are excluded. Lab results and EKG's done in hospitals are excluded and found in the EKG and Labs & Cultures sub-section. In an alternative embodiment, the above excluded information is cross-referenced to the appropriate sub-sections.

Sub-section 10. The EKGs sub-section includes Electrocardiogram, ECG, or rhythm strips.

Sub-section 11. The Imaging Reports sub-section includes scans and ultrasounds including the following imaging results: X-Rays, Ultrasounds, Mammograms, CAT or CT scans, MRI scans, Nuclear medicine scans, DEXA (bone density) scans, PET scans and any other imaging test results.

Sub-section 12. The Special Tests sub-section includes any tests that are non-EKG and non-imaging related, such as: ECHO-Cardiograms, Cardiac stress tests, Treadmill tests, Pulmonary Function tests, Dobutamine or Persantine stress tests, MUGAs, and any other specialized test results.

Sub-section 13. The Labs & Cultures sub-section includes: Blood chemistries, complete blood counts, protimes and other tests of coagulation, arterial blood gases, urinalysis and urine chemistries, lipids, serologic tests, HIV tests (provided with patient's authorization), culture & sensitivities (including urine, sputum, blood, etc.), pathology reports, and any other lab or culture results.

Sub-section 14. The Therapy Notes sub-section includes any kind of log or notes pertaining to any kind of ongoing or periodic therapy or treatment, such as physical therapy, occupational therapy, radiation therapy, chemotherapy, any other therapy notes.

Sub-section 15. The Billing & Insurance sub-section includes copies of insurance cards and other information related to billing, insurance, and payment.

Sub-section 16. The Other sub-section includes record release forms, duplicate, irrelevant, misfiled, section, title, blank, and administrative pages that are not billing, insurance, or prescription related. Other administrative pages can include patient-sent or initiated letters, correspondences, forms, phone logs, record release forms.

The Medical Summary (MS) report enables both patient and doctor to quickly review a patient's medical condition and history both in medical emergency and in less urgent but time sensitive situations such as a first visit to a new doctor. It includes clinical record pages selected from a patient's combined medical record file. The section and sub-sections are given in Table 3 below.

TABLE 3

| SECTION | SUB-SECTION |
|---|---|
| A. Table of Contents | |
| B. Patient Inputs | |
| C. Document Log | |
| | 1. By Date |
| | 2. By Type |
| | 3. By Specialty |
| E. Select Clinical Pages | |
| | 1. Medications & Allergies |
| | 2. Immunizations |
| | 3. Physical Exams |
| | 4. Progress Notes |
| | 5. Consultations |
| | 6. Operative Notes |
| | 7. ER Reports |
| | 8. Hospital Summaries |
| | 9. EKGs |
| | 10. Imaging Reports |
| | 11. Special Tests |
| | 12. Labs & Cultures |
| | 13. Therapy Notes |
| | 14. Patient Added Pages |

The first three sections, Table of Contents, Patient Inputs, and Document Log are the same as those in CMR. The "Select Clinical Pages" sub-section however has specific record pages from the CMR organized into sub-sections based on commonly used medical categories (the MS sub-sections are given in FIG. 15 column 918). For all sub-sections, pages included in each sub-section are automatically drawn from a patient's Combined Medical Records using a formula. The formula includes all documents with document creation dates within the N1 months prior to and including the patient's most recent date of activity for the specific sub-category or a minimum of M1 documents (regardless of time) each with an unique combination of creation date and creator name (author), which ever is greater. In one embodiment N1=12 and M1=3, but N1 and M1 can be any integer numbers. This formula is automatic and captures the most recent pages. However, other embodiments can use a different formula. For example the availability factor can be used to change the order of some documents with the most recent and most available being first.

In another embodiment, the first step in generating the group of selected clinical pages for each sub-section of the MS from the CMR is to retrieve from the DocumentLog table of the database the date of the most recent clinical page for the specified sub-section and target patient. In the second step, the number of Private clinical pages (clinical pages that the patient has designated to be viewable by the patient and no one else), the number of patient-provided clinical pages (clinical pages obtained directly from the patient rather than directly from a healthcare provider), and the total number of clinical pages with author (doctor/organization) creation dates within N2 months prior to and inclusive of the most recent clinical page obtained in the first step above, are obtained from the database. If the second step identifies less than M2 number of clinical pages, the next most recent clinical documents (i.e., over one year of the most recent clinical page) are added to the group so that there are at least M2 unique set of documents presented in the group. In an embodiment N2=12 and M2=3, but N2 and M2 can be any integer numbers. Next, the Availability and Source factors are calculated. The selected clinical pages in the presentation group are now retrieved from the database in reverse chronological order for the specified sub-section. This process is repeated for each sub-section of the "Select Clinical Pages" section.

The "Selected Clinical Pages" has sub-sections given in Table 3 above, and except for a new "Patient Added Pages" sub-section, is a subset of the sub-sections given for the "Clinical Pages" section of the CMR listed in Table 2 above.

The "Patient Added Pages" sub-section includes any clinical pages from the CMR that a patient would view as important to include in the Medical Summary. These pages are usually those pages that fall outside the range set by the automated formula for extracting selected record pages from the CMR.

In one embodiment of the present invention there are two flexible access plans for third parties having on-line access to a patient's medical records: emergency and non-emergency access.

In the case of a medical emergency, a healthcare provider can view the telephone number on the patient's membership card to call the phone server 350 (FIG. 5) with the patient's "Member ID". The amount of access given to the emergency healthcare provider has been pre-selected by the patient to be one of several possible Emergency Access levels. In one embodiment these could be Private (where no information is provided); Contact Information Only (where only contact information for reaching the patient's doctor(s) and/or family members or next-of-kin are made available; Medication and Contacts Only (where medication descriptions and medication lists are added to contact information); and Full Access (where record pages from Combined Medical Records or Medical Summary are made available (except pages member classified as "Private").

Under non-emergency, i.e., normal situations, a patient selects what type of access to give to a third party, such as his doctor, in acessing his medical information. There may be various levels of access for a patient and potentially third-parties authorized by the patient. The access in one embodiment is set using a password protected Web page. The levels in one embodiment are given in Table 4 below.

TABLE 4

| | Access Rights | | | |
|---|---|---|---|---|
| Access Levels | Assign (create) new users to access patient's account? | Schedule a specific time for viewing patient's medical records online? | Edit patient's records and distribute records to another party? | View patient's classified "Private" pages? |
| Patient | YES | YES | YES | YES |
| Surrogate | YES | YES | YES | NO |
| Provider | NO | YES | NO | NO |
| Limited | NO | NO(*) | NO | NO |

(*)In one embodiment the patient must schedule a session for the third party.

The patient or his legal surrogate decides and authorizes the distribution of all or part of the patient's medical records to one or more third parties. A patient can transmit, via email or fax, a medical record or a group of medical records directly by using her web browser. Off-line distribution service is provided only with a patient's, legal surrogate or guardian's signed authorization on a "Send To" Authorization Form. There are several media which the whole or portion of a patient's CMR or MS report can be distributed by, to include: fax, email, CD-ROM, DVD, paper copy, or microfiche.

Figures 1, 20:
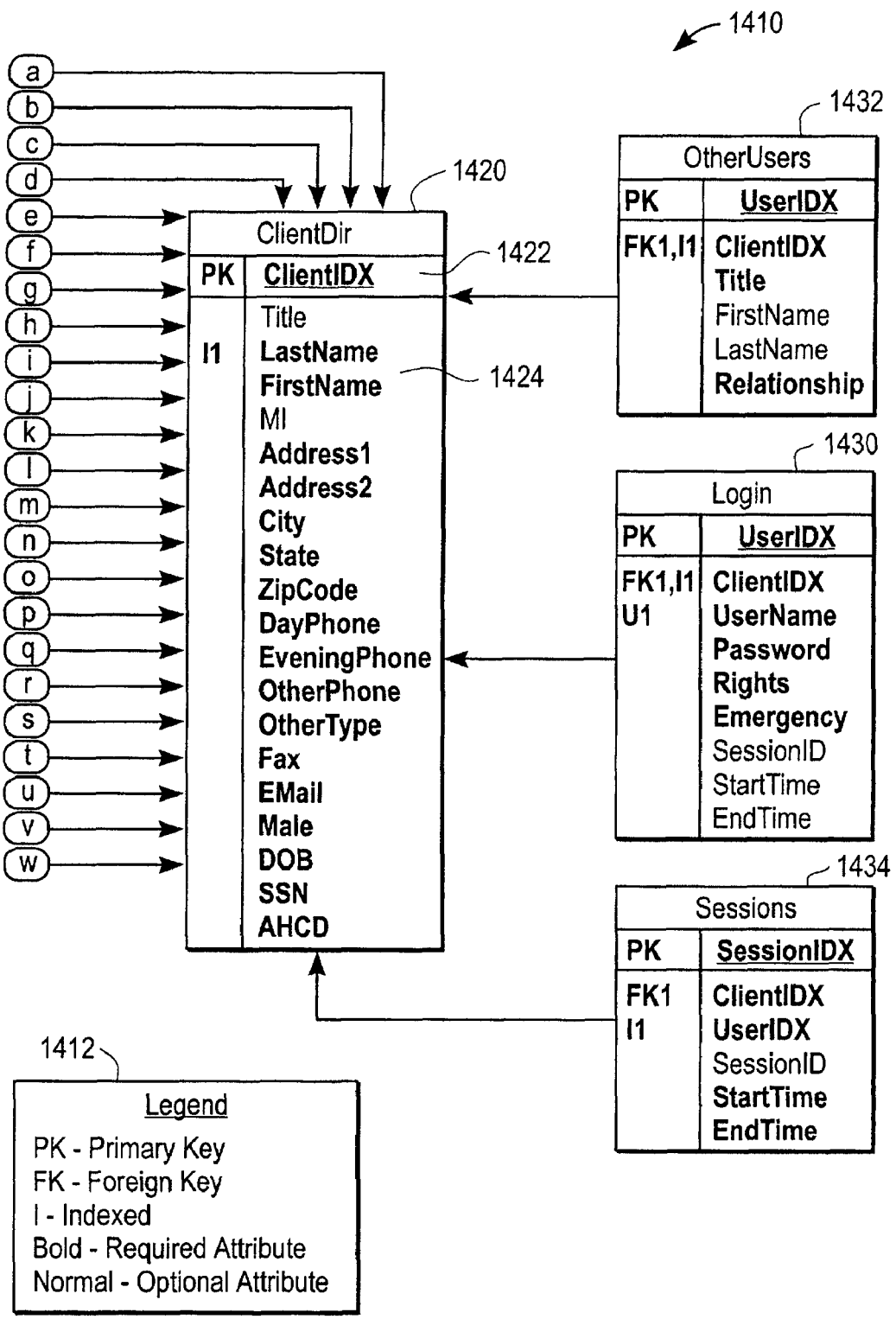
Figures 2, 20:
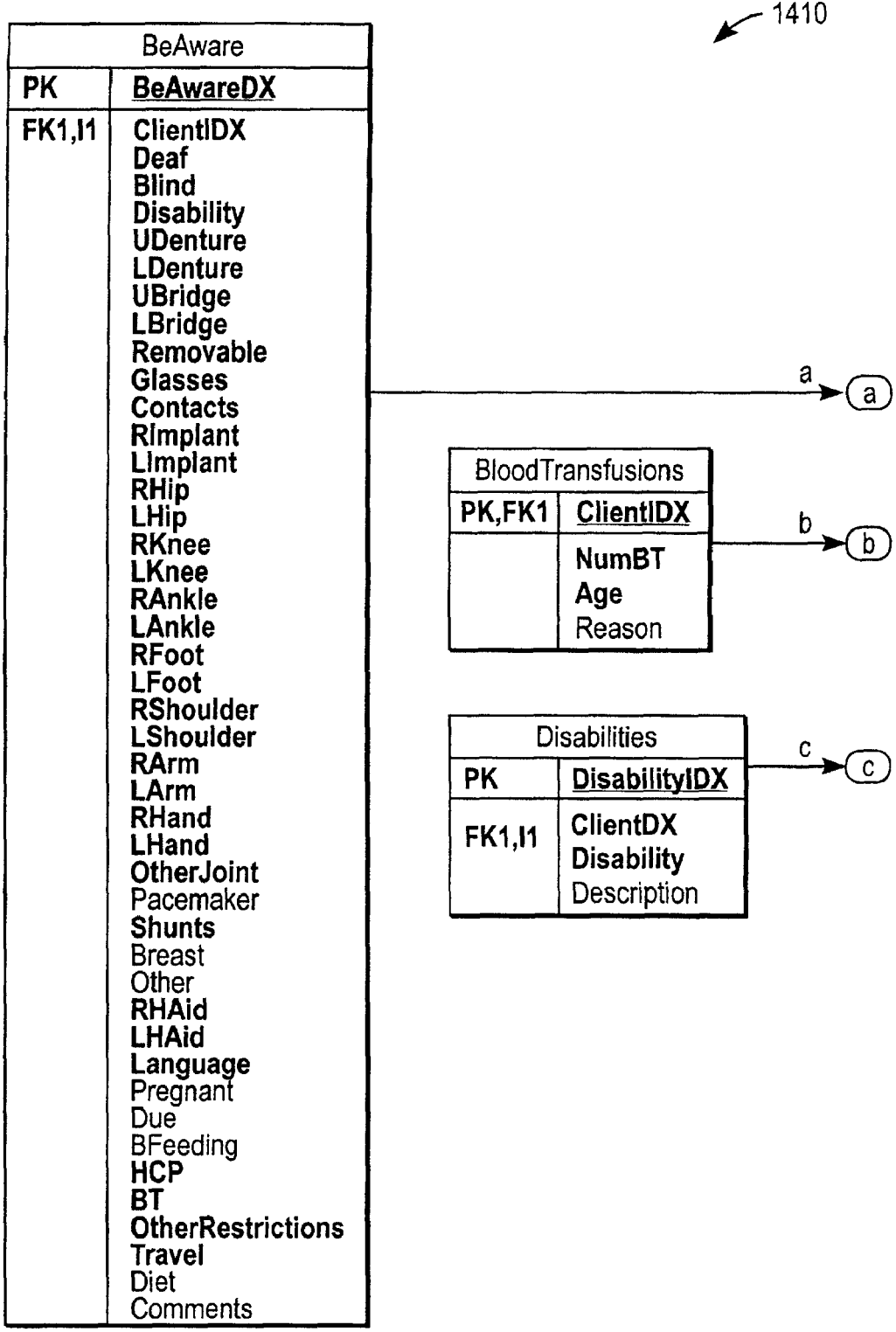
Figures 3, 20:
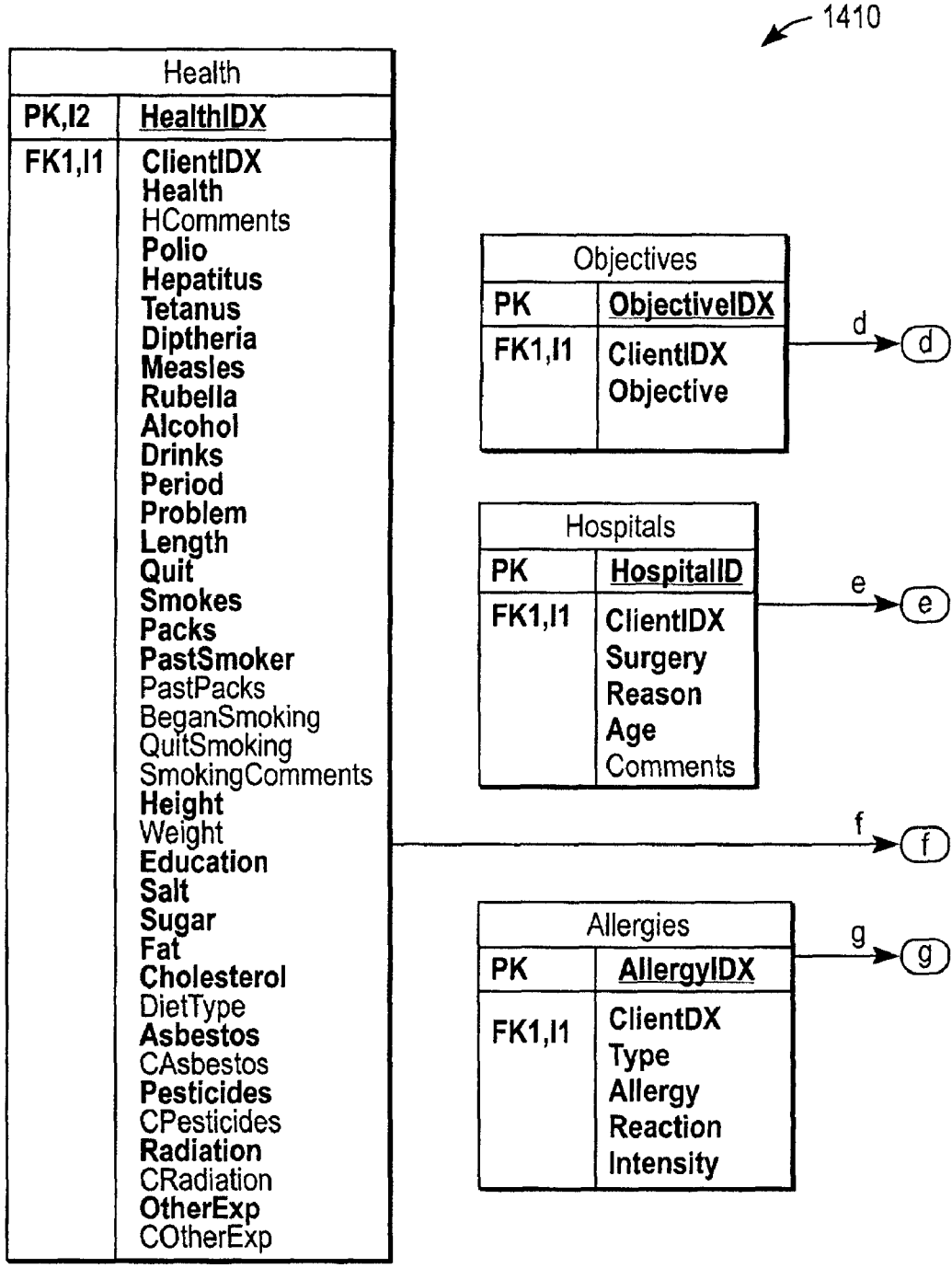
Figures 4, 20:
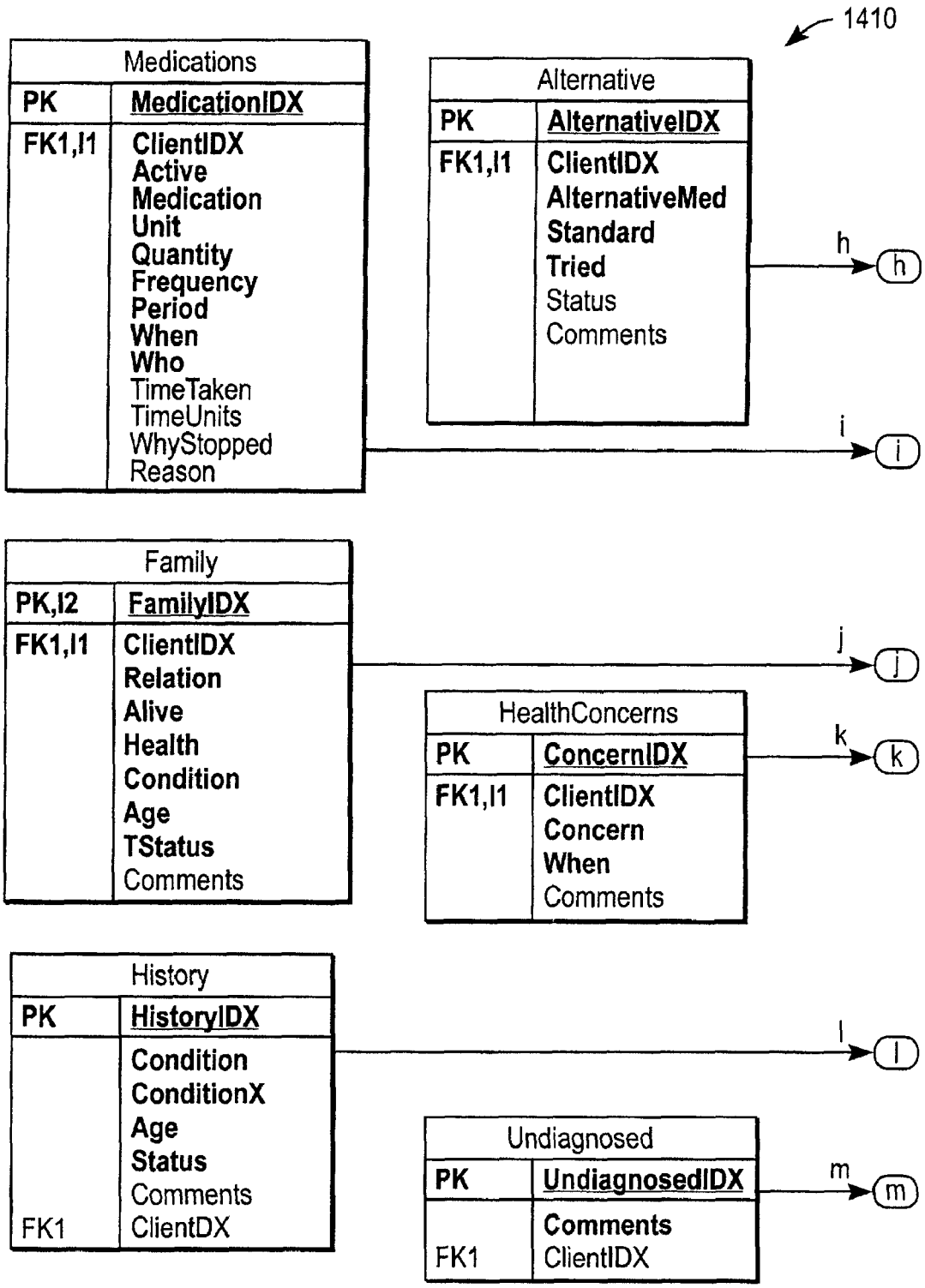
Figures 5, 20:
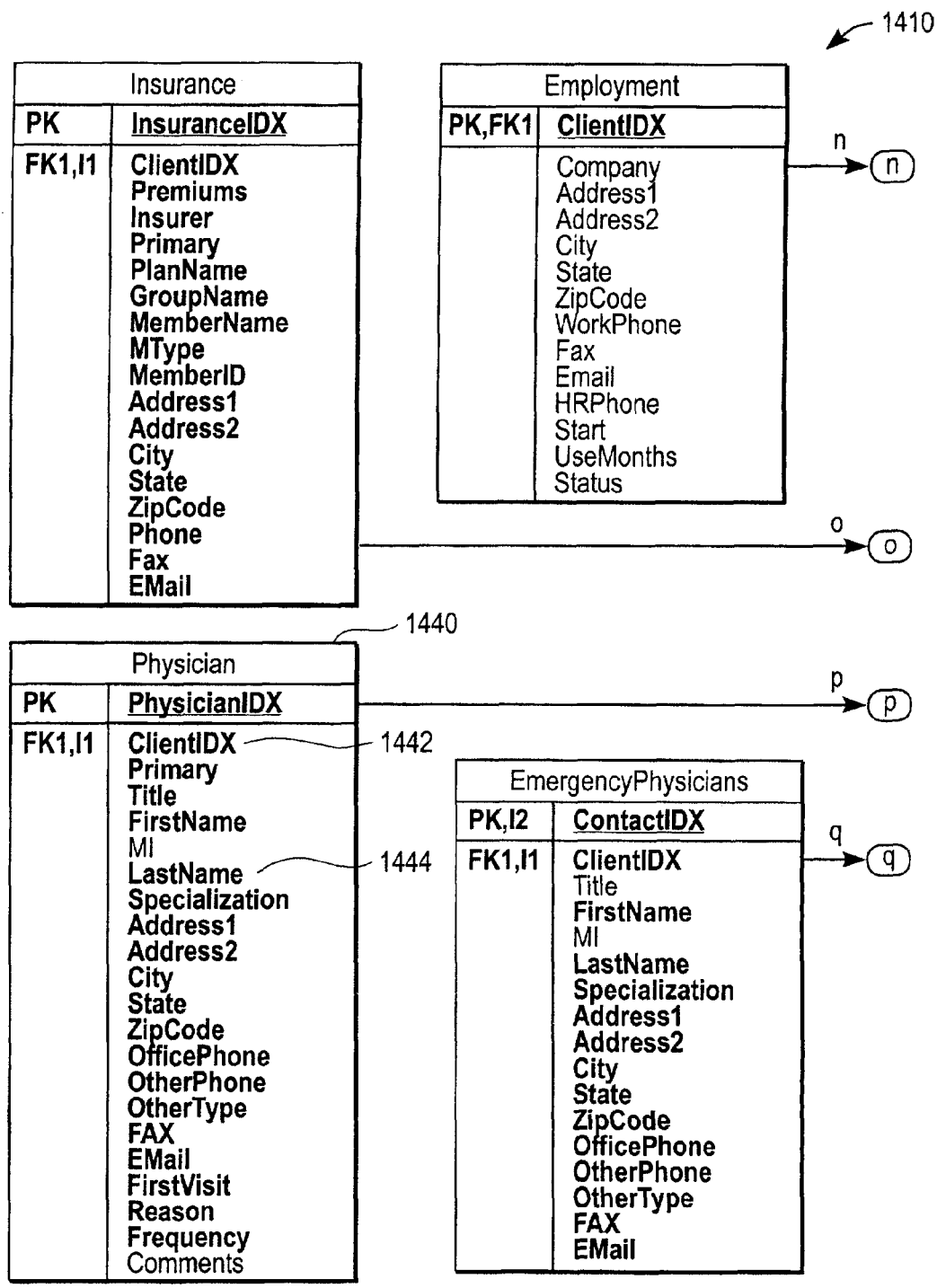
Figures 6, 20:
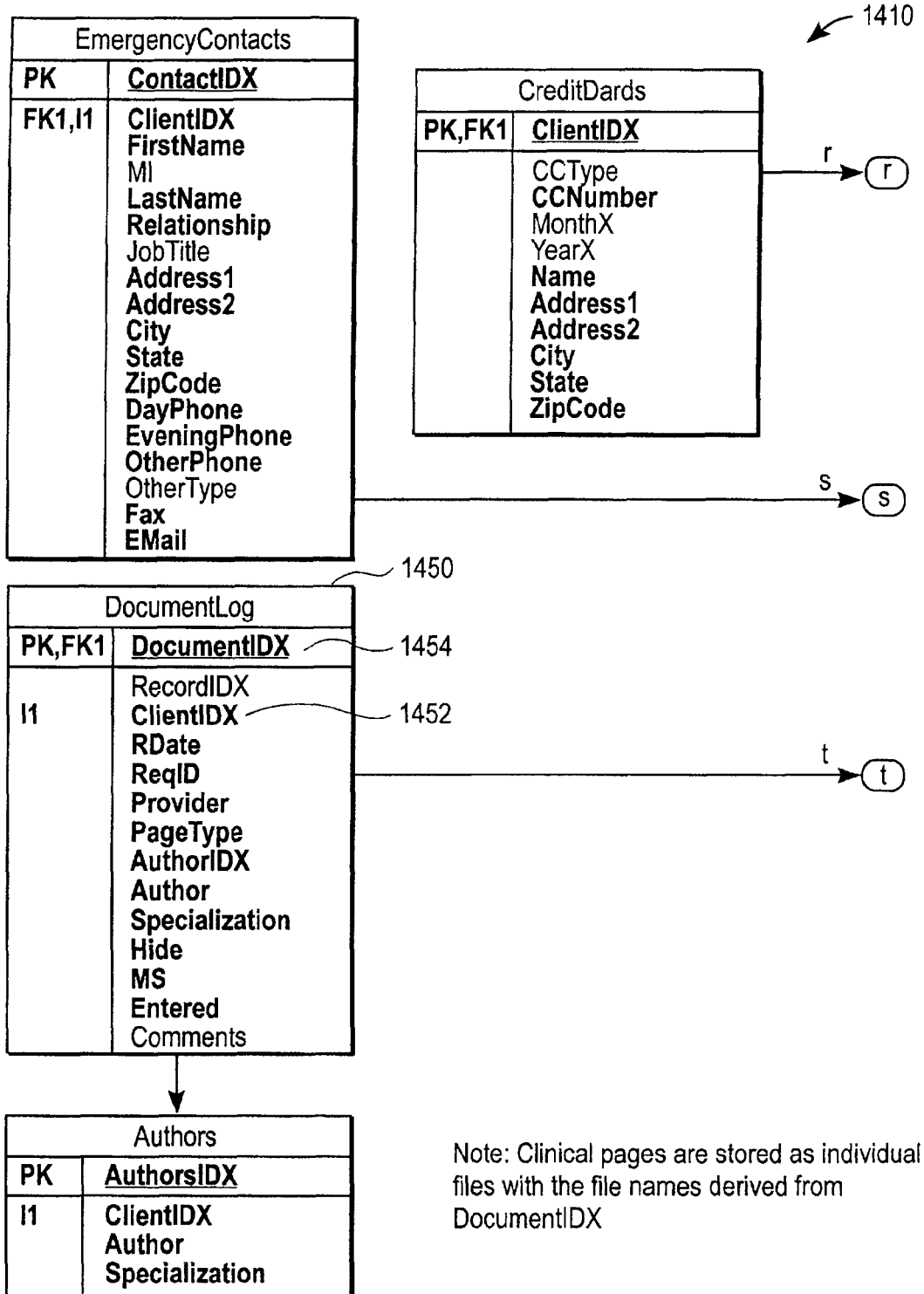
Figures 7, 20:
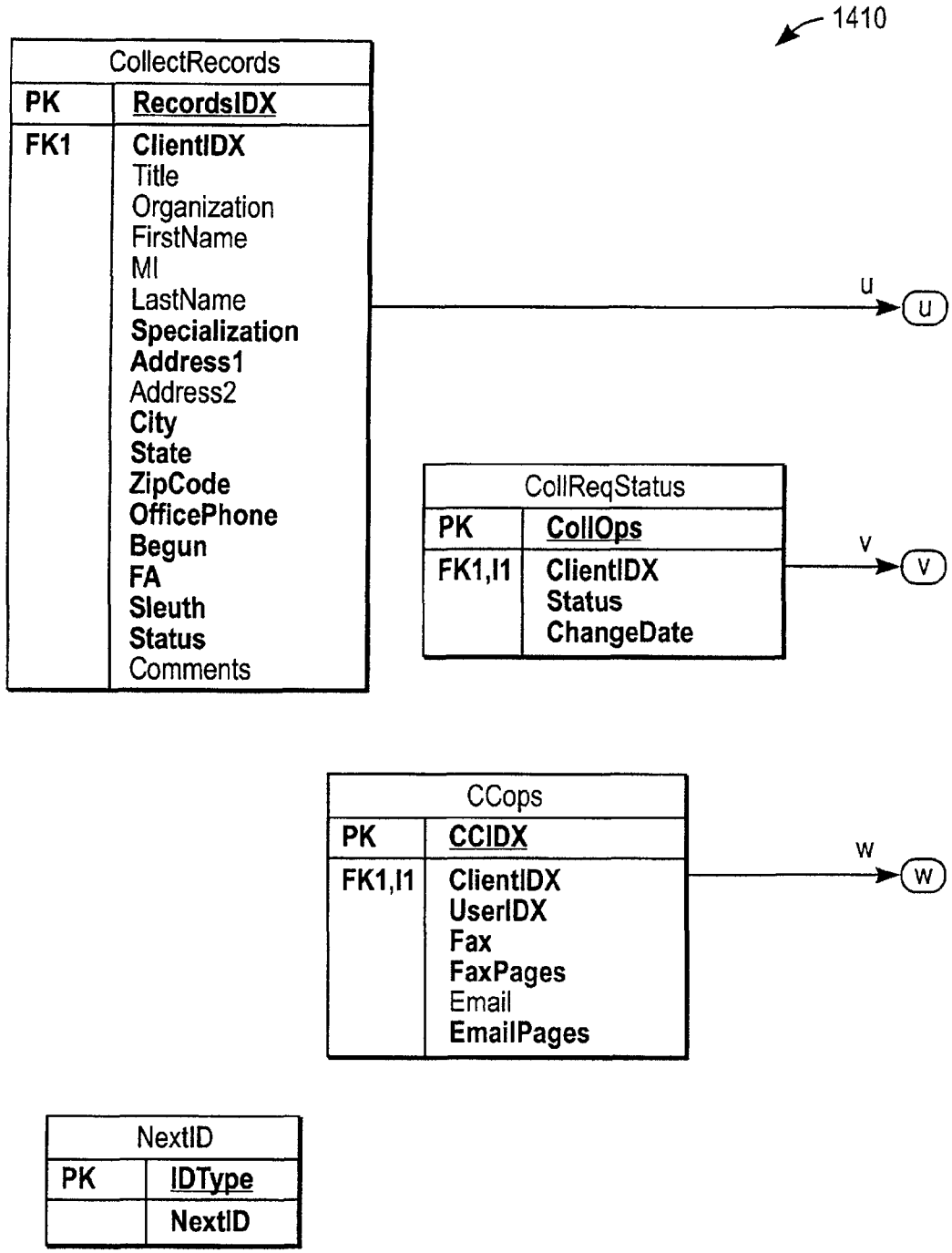

FIGS. 20-1 to 20-7 show the database structure 1410 of an embodiment of the present invention. The off-page connectors are given by the letters "a" through "w". The legend 1412 in FIG. 20-1 explains that "PK" is a primary key, "FK" is a foreign key, and "I" is indexed (i.e., an index structure is used to access records in a file). While in legend 1412, "bold" text indicates a required attribute and "normal" text indicates an optional attribute in this embodiment, other embodiments have different combinations of required and optional attributes. An example of an entity set is "ClientDir" entity 1420 (i.e., the set of clients or patients) which has a primary key of "ClientIDX" (i.e., the client ID) 1422, and several attributes, e.g., "LastName" 1424 (i.e., the client's last name). A particular value of "ClientIDX" 1422 can be used to determine the client's (i.e., patient's) physician, by using the foreign key "ClientIDX" 1442 in "Physician" entity set 1440 in FIG. 20-5, to retrieve attribute "LastName" 1444 of the entity (i.e., a particular doctor) in the "Physician" entity set 1440 with the particular value of "ClientIDX" (i.e., the last name of the patient's doctor). The off page connector "p" from entity set 1440 terminates in ClientDir entity 1420 indicating the foreign key relationship. In addition, the particular value of "ClientIDX" can be used to search entity set "DocumentLog" 1450 (i.e., the set of document logs) to get the "DocumentIDX" 1454 (e.g., Document ID #) for each document associated with the client with the particular value of "ClientIDX" (i.e., the document IDs of the documents in a patient's medical records). The off page connector "t" from entity set 1450 terminates in ClientDir entity 1420 indicating the foreign key relationship.

While the embodiments given herein describe management of a patient's medical records, the scope of the present invention is not so limited but, includes other types of records where a person needs his/her records collected, categorized, stored (under his/her direction), and presented (e.g., displayed or distributed). Such other type of records include tax documents, wills, personal letters, legal papers, licensing/ownership papers, bills, payments, investments, and other personal information.

Although specific embodiments of the invention have been described, various modifications, alterations, alternative constructions, and equivalents are also encompassed within the scope of the invention. The described invention is not restricted to operation within certain specific data processing environments, but is free to operate within a plurality of data processing environments. Additionally, although the invention has been described using a particular series of transactions and steps, it should be apparent to those skilled in the art that the scope of the invention is not limited to the described series of transactions and steps.

Further, while the invention has been described using a particular combination of hardware and software, it should be recognized that other combinations of hardware and software are also within the scope of the invention. The invention may be implemented only in hardware or only in software or using combinations thereof.

The specification and drawings are, accordingly, to be regarded in an illustrative rather than a restrictive sense. It will, however, be evident that additions, subtractions, deletions, and other modifications and changes may be made thereunto without departing Further, at least the following concepts have been presented by the present description.

Concept 1. A method for managing a patient's medical records authored by a plurality of healthcare providers, wherein at least two healthcare providers of said plurality have different medical records systems, said method comprising:

collecting a plurality of medical records from a plurality of healthcare providers identified by the patient, wherein said collecting is by a service provider in response to a request by the patient for said collecting of said plurality of medical records;

making a substantially unaltered copy in electronic image format of each document in the patient's collected medical records;

categorizing a plurality of said substantially unaltered copied documents according to a categorization system, such that each said substantially unaltered copied document is identified by a unique document identifier;

storing in a central storage area said categorized plurality of substantially unaltered copied documents, wherein said central storage area comprises a database, and wherein access to said categorized plurality of substantially unaltered copied documents in said central storage area must be authorized by said patient; and retrieving from said central storage area an ordered set of documents of said categorized plurality of substantially unaltered copied documents, using at least one of a plurality of predetermined criteria.

Concept 2. The method of concept 1 wherein each said copied document is uniquely identified.

Concept 3. The method of concept 1 wherein said plurality of predetermined criteria include sorting said categorized plurality of substantially unaltered copied documents in reverse chronological order of creation dates, by medical sub-category, by author, by author specialization, in numerical order of said document identifier, by document provider, or any combination thereof.

Concept 4. The method of concept 1 further comprising:
sorting said plurality of substantially unaltered copied documents; and
presenting said sorted plurality of substantially unaltered copied documents based on a selection criterion and a prioritization algorithm.

Concept 5. The method of concept 1 further comprising displaying said ordered set of said categorized plurality of substantially unaltered copied documents to a current healthcare provider examining said patient.

Concept 6. The method of concept 5 wherein said displaying said ordered set of said categorized plurality of substantially unaltered copied documents to a current healthcare provider occurs only for substantially unaltered copied documents in said ordered set which are not marked private by said patient.

Concept 7. The method of concept 1 wherein said categorization system is the same for all healthcare providers of said plurality of healthcare providers.

Concept 8. The method of concept 1 wherein said categorization system comprises a plurality of categories, said categories comprising the document identifier.

Concept 9. The method of concept 8 wherein said categories further comprise: an author of a page, a specialization of said author, a date said page was created, a page type, a record source, or a name of a file provider.

Concept 10. The method of concept 1 wherein said plurality of substantially unaltered copied documents comprises scanned paper-based pages of said patient's medical records.

Concept 11. A method for a patient accessing said patient's medical records originating from a plurality of healthcare providers, wherein at least two healthcare providers of said plurality have different medical records systems, said method comprising:
collecting from said plurality of healthcare providers at the request of the patient a plurality of substantially unaltered copied documents of said patient's medical records, wherein said plurality of healthcare providers comprise a past and a present health care provider of said patient, wherein the patient identifies the plurality of healthcare providers to a service provider, and wherein said collecting is performed by the service provider, said collecting including the steps of (1) the service provider contacting said plurality of healthcare providers to request said plurality of substantially unaltered copied documents of said patient's medical records and (2) the service provider receiving said plurality of substantially unaltered copied documents of said patient's medical records from said plurality of healthcare providers;
categorizing said plurality of substantially unaltered copied documents according to a categorization system, having more than two categories, wherein said categorizing includes categorizing each substantially unaltered copied document in the patient's collected medical records;
storing in a storage area of a central computer storage said categorized plurality of substantially unaltered copied documents, wherein said central storage area comprises a database, and wherein access to said categorized plurality of substantially unaltered copied documents in said storage area is under the control of said patient; and
retrieving a document of said stored categorized plurality of substantially unaltered copied documents according to at least one of a plurality of selection criteria, said plurality of selection criteria based on said categorization system.

Concept 12. The method of concept 11 further comprising displaying said retrieved document to said patient.

Concept 13. The method of concept 11 further comprising displaying said retrieved document to a third party after approval by said patient or said patient's legal surrogate.

Concept 14. The method of concept 11 further comprising displaying said retrieved document to said patient, but not to said patient's legal surrogate.

Concept 15. The method of concept 11 further comprising distributing said retrieved document by fax, email, or hard copy.

Concept 16. The method of concept 15 wherein said hard copy comprises a floppy disk, CD, microfiche, or paper copy.

Concept 17. The method of concept 11 wherein said one selection criterion selects documents of said stored categorized plurality of substantially unaltered copied documents with document dates within the previous N months starting with said patient's most recent date of activity or a minimum of M documents, whichever results in more documents.

Concept 18. The method of concept 17 wherein N=12 and M=3.

Concept 19. The method of concept 11 wherein said categorization system is the same for all healthcare providers of said plurality of healthcare providers.

Concept 20. The method of concept 11 further comprising displaying a document log of said categorized plurality of substantially unaltered copied documents to said patient.

Concept 21. The method of concept 20 wherein said document log is organized by document date, page type, or doctor specialty.

Concept 22. The method of concept 11 wherein said selection criteria selects documents in a category selected from a group of categories consisting of: Medications & Allergies, Immunizations, Patient Intake Apps, Physical Exams, Progress Notes, Consultations, Operative Notes, ER Reports, Hospital Summaries, EKGs, Imaging Reports, Special Tests, Labs & Cultures, Therapy Notes, Billing & Insurance, and Other.

Concept 23. The method of concept 11 wherein said selection criteria selects documents in a category selected from a group of categories consisting of: Medications & Allergies, Immunizations, Physical Exams, Progress Notes, Consultations, Operative Notes, ER Reports, Hospital Summaries, EKGs, Imaging Reports, Special Tests, Labs & Cultures, Therapy Notes, and Patient Added Pages.

Concept 24. The method of concept 11 wherein said categorization system comprises a plurality of categories, said plurality of categories comprising: document ID, page type, author of said document, specialization of said author, provider of the record, and date of said document.

Concept 25. The method of concept 24 wherein said selection criteria selects documents in a category of said plurality of categories.

Concept 26. The method of concept 11 further comprising, when needed, converting to electronic format each substantially unaltered copied document of said patient's medical records.

Concept 27. The method of concept 11 further comprising, providing to said patient a Combined Medical Records (CMR) report, said CMR report comprising said categorized substantially unaltered copied documents organized by sections, said sections comprising a clinical pages section.

Concept 28. The method of concept 27 wherein said clinical pages section comprises Medications & Allergies, Immunizations, Patient Intake Apps, Physical Exams, Progress Notes, Consultations, Operative Notes, ER Reports, Hospital Summaries, EKGs, Imaging Reports, Special Tests, Labs & Cultures, Therapy Notes, Billing & Insurance, and Other sub-sections.

Concept 29. The method of concept 11 further comprising, providing to said patient a Medical Summary (MS) report, said MS report comprising said categorized substantially unaltered copied documents organized by sections, said sections comprising a selected clinical pages section.

Concept 30. The method of concept 29 wherein said selected clinical pages section comprises Medications & Allergies, Immunizations, Physical Exams, Progress Notes, Consultations, Operative Notes, ER Reports, Hospital Summaries, EKGs, Imaging Reports, Special Tests, Labs & Cultures, Therapy Notes, and Patient Added Pages sub-sections.

Concept 31. The method of concept 11 further comprising, searching for a doctor's location using a customized search engine.

Concept 32. A method for a patient accessing said patient's medical records originating from a plurality of healthcare providers, said method comprising:

collecting from said plurality of healthcare providers at the request of the patient said patient's medical records, wherein the patient identifies the plurality of healthcare providers to a service provider, and wherein said collecting is performed by the service provider, said collecting including the steps of (1) the service provider contacting said plurality of healthcare providers to request said patient's medical records and (2) the service provider receiving said patient's medical records from said plurality of healthcare providers;

categorizing a plurality of substantially unaltered copied documents of said patient's medical records according to a categorization system, wherein said categorizing includes categorizing each substantially unaltered copied document in the patient's collected medical records;

storing in a storage area of a central computer storage said categorized plurality of substantially unaltered copied documents, wherein said central computer storage comprises a database, and access to said categorized plurality of substantially unaltered copied documents in said storage area under the control of said patient; and displaying a document log of said categorized plurality of substantially unaltered copied documents to said patient.

Concept 33. The method of concept 32 further comprising displaying a time line graph indicating a date when a document of said categorized plurality of substantially unaltered copied documents was created.

Concept 34. The method of concept 32 wherein said document log comprises an inventory of said categorized plurality of substantially unaltered copied documents sorted by document ID, page type, author of said document, specialization of said author, record provider, or document date.

Concept 35. The method of concept 32 wherein said document log is sorted by date in reverse chronological order.

Concept 36. The method of concept 32 wherein said document log comprises a link to a display of a document of said categorized plurality of substantially unaltered copied documents.

Concept 37. A system for centrally managing a plurality of medical records of a patient distributed across a plurality of healthcare providers, said system comprising:

a collection module for collecting from said plurality of healthcare providers at the request of the patient said plurality of medical records, wherein the patient identifies the plurality of healthcare providers to a service provider, wherein the service provider contacts said plurality of healthcare providers to request said plurality of medical records and receives said plurality of medical records from said plurality of healthcare providers, and wherein said collection module is other than the patient;

a computerized categorization system for categorizing substantially unaltered copied documents of said plurality of medical records, wherein said categorization system is the same for all healthcare providers of said plurality of healthcare providers;

a patient directed central storage area wherein said central storage area comprises a database for electronically storing said categorized substantially unaltered copied documents of said plurality of medical, wherein the patient controls the scope of access to the patient's stored substantially unaltered copied documents; and a retrieval module for retrieving an ordered plurality of documents of said categorized substantially unaltered copied documents of said plurality of medical records, wherein said ordered plurality of documents is arranged using at least one of a plurality of criteria, said plurality of criteria based on said computerized categorization system.

Concept 38. The system of concept 37 further comprising a display for displaying said ordered plurality of documents.

Concept 39. The system of concept 38 wherein said display for presenting comprises a Web browser.

Concept 40. The system of concept 37 further comprising a distribution module for creating a CD, email, facsimile document, or printed document comprising information in said ordered plurality of documents.

Concept 41. The system of concept 37 further comprising a search engine application stored in a computer readable medium for locating a doctor or an organization of said plurality of healthcare providers.

Concept 42. The system of concept 37 wherein said categorization system comprises: document ID, page type, author of said document, specialization of said author, provider of the record, and date of each said substantially unaltered copied document.

Concept 43. A method of centrally managing medical records of a patient authored by a plurality of healthcare providers, said method comprising:

collecting from said plurality of healthcare providers at the request of the patient a plurality of medical records, wherein said plurality of medical records comprise a plurality of paper based documents, and wherein said plurality of healthcare providers comprise a past and a current health care provider, wherein the patient identifies the plurality of healthcare providers to a service provider, and wherein said collecting is performed by the service provider;

classifying each page of said plurality of paper based documents using classes of a classification system common across said plurality of healthcare providers;

converting each page of said plurality of paper based documents to a substantially unaltered electronic image;

storing each substantially unaltered electronic image in a computer storage readable medium wherein access to said computer storage readable medium is authorized by said patient;

retrieving an organized subset of said substantially unaltered electronic images, using at least one of a plurality of criteria; and displaying an electronic image of said organized subset.

Concept 44. The method of concept 43 wherein said classifying each page comprises adding a header and a footer to each page, wherein said header comprises a first group of classes of said classification system and said footer comprises a second group of classes of said classification system.

Concept 45. The method of concept 44 wherein said first group comprises: a document ID, page type, patient name, and member ID.

Concept 46. The method of concept 45 wherein said page type is a medical category selected from a group consisting of: Medications & Allergies, Immunizations, Patient Intake Apps, Physical Exams, Progress Notes, Consultations, Operative Notes, ER Reports, Hospital Summaries, EKGs, Imaging Reports, Special Tests, Labs & Cultures, Therapy Notes, Billing & Insurance, and Other.

Concept 47. The method of concept 44 wherein said second group comprises: author of said page, author's specialization, if a doctor, and creation date of said page.

Concept 48. The method of concept 43 wherein said classification system comprises: a document ID, page type, patient name, member ID, author of said page, author's specialization, if a doctor, and creation date of said page.

Concept 49. A system for centrally managing a plurality of medical records of a patient originating from a plurality of healthcare providers, said system comprising:

a backend server for receiving said plurality of medical records, each medical record comprising a plurality of documents, from said plurality of healthcare providers, wherein each document of said plurality of medical records is categorized, wherein the patient identifies the plurality of healthcare providers to a service provider, and wherein said plurality of medical records are collected by the service provider in response to a request by the patient for the collecting, wherein the service provider contacts said plurality of healthcare providers to request said plurality of medical records and the service provider receives said plurality of medical records from said plurality of healthcare providers;

a database connected to said backend server for storing said categorized documents, wherein access to said categorized documents is controlled by said patient; and a Web server connected to said backend server and to a client system, wherein said Web server processes a search request by said client system for retrieving a set of ordered documents of said categorized documents, said set arranged by using at least one of a plurality of criteria.

Concept 50. The system of concept 49 further comprising a scanner coupled to said backend server for converting a paper-based document of said plurality of medical records to an electronic image for storing in said database.

Concept 51. The system of concept 49 further comprising a search engine for locating a healthcare provider of said plurality of healthcare providers.

Concept 52. The system of concept 49 further comprising a window displaying a current collection status of a patient's medical records from a healthcare provider of said plurality of healthcare providers.

Concept 53. A method in a computer system for displaying a document log of a plurality of medical records of a patient, comprising: displaying a table comprising a plurality of rows, wherein each row comprises a plurality of columns, wherein a column of said plurality of columns comprises a plurality of cells associated with a category of a plurality of categories; and displaying document ID data in a cell of said plurality of cells of a row of said plurality of rows, wherein said document ID data identifies a document in said plurality of medical records.

Concept 54. The method of concept 53 wherein said plurality of categories comprises: document ID, page type, author of said document, specialization of said author, provider of the record, and date of said document.

Concept 55. The method of concept 53 wherein said document ID data comprises a hyperlink to an electronic image of said document, and wherein, when said hyperlink is selected, said electronic image is displayed.

Concept 56. A method, using a computer, for enabling a patient to comment on a medical record of said patient, comprising: searching for an electronic image of said medical record using a category assigned to said medical record, said electronic image stored in a database, wherein access to said electronic image is controlled by said patient; receiving a patient's comments; and electronically linking said patient's comments with said electronic image.

Concept 57. The method of concept 56 further comprising displaying said patient's comments concurrently with said electronic image.

Concept 58. The method of concept 56 further comprising storing in said database said patient's comments, and retrieving said patient's comments, when said electronic image is displayed.

Concept 59. The method of concept 56 wherein said category is selected from a group consisting of document ID, page type, patient name, member ID, author of said document, specialization of said author, provider of the record, and creation date of said document.

Concept 60. The method of concept 56 further comprising: receiving a doctor's comments; and electronically linking said doctor's comments with said electronic image.

Concept 61. A method in a computer system for displaying to a patient a document timeline of a plurality of documents in a patient's medical records, comprising: displaying a first axis having sequential calendar time units; displaying a second axis listing said plurality of documents; and providing an indication along said first axis of a creation date of at least one of said plurality of documents.

Concept 62. The method of concept 61 wherein said indication on said first axis includes a name of an author of said document and said date of creation.

Concept 63. The method of concept 61 wherein said listing of said plurality of documents is by medical sub-categories.

Concept 64. The method of concept 61 wherein a document of said plurality of documents comprises a document identifier, said document identifier comprising a hyperlink to an electronic image of said document, and wherein, when said hyperlink is selected, said electronic image is displayed.

Concept 65. The method of concept 61 wherein said calendar time unit is selected from a group consisting of day, month, and year.

Concept 66. A method in a computer system for displaying a progress note timeline of a plurality of progress notes in a patient's medical records, comprising: displaying a first axis indicating sequential calendar time units; displaying a second axis indicating a total number of said plurality of progress notes for each sequential calendar time unit; and providing an indication along said first axis of said total number of said plurality of progress notes with creation dates in a calendar time unit of said sequential calendar time units.

Concept 67. The method of concept 66 wherein said calendar time unit is selected from a group consisting of day, month, and year.

Concept 68. A method for using a patient's medical records by a doctor, comprising clinical pages, stored in a patient directed computer storage area, said method comprising: said doctor selecting a category of a plurality of categories categorizing said clinical pages; retrieving from said computer storage area a subset of clinical pages, wherein said subset comprises a plurality of clinical pages belonging to said category and not designated private by said patient; calculating an availability factor, wherein said availability factor is a ratio of a number of clinical pages belonging to said subset to a total number of clinical pages belonging to said category; and displaying said availability factor to said doctor for use in evaluating completeness of said subset.

Concept 69. The method of concept 68 wherein said plurality of categories comprise a plurality of medical sub-categories of a page type category.

Concept 70. A method for using a patient's medical records by a doctor, comprising clinical pages from a healthcare provider, stored in a patient directed computer storage area, said method comprising: said doctor selecting a category of a plurality of categories categorizing said clinical pages; retrieving from said computer storage area a subset of clinical pages belonging to said category; calculating a source factor, wherein said source factor is a ratio of a number of clinical pages in said subset obtained directly from said healthcare provider to a total number of clinical pages in said subset; and displaying said source factor to said doctor for use in evaluating reliability of said subset.

Concept 71. The method of concept 70 wherein said plurality of categories comprise a plurality of medical sub-categories of a page type category.

Concept 72. The method of concept 70 wherein said total number of clinical pages in said subset is a sum of clinical pages in said subset obtained directly from said healthcare provider plus clinical pages in said subset obtained via said patient.

Concept 73. The method of concept 1 further comprising; receiving a record collection request from the patient for collecting the plurality of medical records from the plurality of health care providers identified by the patient.

Concept 74. The method of concept 10, wherein said scanned paper-based pages include handwritten notes of a healthcare provider.

Concept 75. The method of concept 11 further comprising: the service provider automatically generating letters for said patient's signature to request said plurality of substantially unaltered copied documents of said patient's medical records.

Concept 76. The method of concept 11 further comprising: the service provider tracking the status of said collecting.

Concept 77. The method of concept 11 further comprising: enabling said patient to add comments to the substantially unaltered copied document in electronic image format.

What is claimed is:

1. A method for managing a patient's medical records authored by at least two healthcare providers, said method comprising:
   collecting at least one medical record from at least two healthcare providers, wherein said collecting is by a service provider;
   making an electronic image of each collected medical record;
   categorizing each electronic image according to a standard set of categories;
   storing in a storage area each categorized electronic image, wherein said storage area comprises a data base; and
   retrieving from said storage area and presenting an ordered set of at least some of the categorized electronic images, using at least one of a plurality of predetermined criteria.

2. The method of claim 1 wherein said plurality of predetermined criteria include sorting categorized plurality of electronic images in reverse chronological order of creation dates, by medical sub-category, by author, by author specialization, in numerical order of document identifier, by document provider, or any combination thereof.

3. The method of claim 1 further comprising:
   sorting a plurality of electronic images; and
   presenting said sorted plurality of electronic images based on a selection criterion and a prioritization algorithm.

4. The method of claim 1 further comprising displaying said ordered set of electronic images to a current healthcare provider examining said patient.

5. The method of claim 4 wherein said displaying said ordered set of electronic images to a current healthcare provider occurs only for electronic images in said ordered set which are not marked private by said patient.

6. The method of claim 1 wherein said standard set of categories is the same for each healthcare provider of a plurality of healthcare providers.

7. The method of claim 1 wherein said standard set of categories comprises a plurality of categories, said categories comprising a document identifier.

8. The method of claim 7 wherein said categories further comprise: an author of a page, a specialization of said author, a date said page was created, a page type, a record source, or a name of a file provider.

9. The method of claim 1 wherein said electronic image comprises a scanned paper-based page of said patient's medical records.

10. The method of claim 9, wherein said scanned paper-based pages include handwritten notes of a healthcare provider.

11. The method of claim 1 further comprising;
    the service provider receiving a medical record collection request from the patient for collecting medical records from at least one health care provider identified by the patient.

12. The method of claim 1 wherein the patient's medical records are authored by a plurality of healthcare providers and at least two healthcare providers of said plurality have different medical record systems.

13. The method of claim 1 wherein collecting the at least one medical record is in response to a request by the patient.

14. The method of claim 1 wherein access to a stored categorized electronic image in said storage area must be authorized by said patient.

15. The method of claim 1 wherein each electronic image is identified by a unique document identifier.

16. The method of claim 15 wherein the document identifier comprises a document name or a document title.

17. A method for a patient accessing said patient's medical records originating from at least one healthcare provider, said method comprising:
    collecting from said at least one healthcare provider at least one electronic image of said patient's medical records, wherein collecting is performed by the service provider, said collecting including the steps of the service provider contacting said healthcare provider to request said at least one electronic image of said patient's medical records and the service provider receiving said at least one electronic image of said patient's medical records from said healthcare provider;
    categorizing each electronic image according to a standard set of categories, having at least two categories;
    storing in a storage area of a computer each said categorized electronic image, wherein said storage area comprises a database; and
    retrieving at least one electronic image of said stored categorized electronic images according to at least one of a plurality of selection criteria, said plurality of selection criteria based on said standard set of categories.

18. The method of claim 17 further comprising displaying or providing said retrieved electronic image to said patient.

19. The method of claim 17 further comprising displaying or providing said retrieved electronic image to a third party after approval by said patient or said patient's legal surrogate.

20. The method of claim 17 further comprising displaying or providing said retrieved electronic image to said patient, but not to said patient's legal surrogate.

21. The method of claim 17 further comprising distributing said retrieved electronic image by fax, email, or hard copy.

22. The method of claim 21 wherein said hard copy comprises a floppy disk, CD, microfiche, or paper copy.

23. The method of claim 17 wherein said standard set of categories is the same for all healthcare providers of said patient.

24. The method of claim 17 further comprising displaying a log of said categorized electronic images to said patient.

25. The method of claim 24 wherein said log is organized by document date, page type, or doctor specialty.

26. The method of claim 17 wherein said plurality of selection criteria comprises: Medications & Allergies, Immunizations, Patient Intake Apps, Physical Exams, Progress Notes, Consultations, Operative Notes, ER Reports, Hospital Summaries, EKGs, Imaging Reports, Special Tests, Labs & Cultures, Therapy Notes, Billing & Insurance, Patient Added Pages and Other.

27. The method of claim 17 wherein said standard set of categories comprises a plurality of categories, said plurality of categories comprising: document identifier, page type, author, specialization of said author, healthcare provider of the record, and date of the record.

28. The method of claim 27 wherein said selection criteria selects electronic images in a category of said plurality of categories.

29. The method of claim 27 wherein the document identifier comprises a document name or a document title.

30. The method of claim 17 further comprising, when needed, converting to electronic format each document of said patient's medical records.

31. The method of claim 17 further comprising, providing to said patient a report, said report comprising said categorized electronic images organized by sections, said sections comprising a clinical section.

32. The method of claim 31 wherein said clinical section comprises Medications & Allergies, Immunizations, Patient Intake Apps, Physical Exams, Progress Notes, Consultations, Operative Notes, ER Reports, Hospital Summaries, EKGs, Imaging Reports, Special Tests, Labs & Cultures, Therapy Notes, Billing & Insurance, and Other sub-sections.

33. The method of claim 17 further comprising the service provider automatically generating letters for said patient's signature to request said plurality of electronic images of said patient's medical records.

34. The method of claim 17 further comprising the service provider receiving a medical record collection request from the patient for collecting medical records from at least one health care provider identified by the patient.

35. The method of claim 17 further comprising enabling said patient to add comments to the electronic images copied document in electronic image format.

36. The method of claim 17 wherein said at least one healthcare provider comprises a past and a current health care provider.

37. The method of claim 17 wherein the patient's medical records are authored by a plurality of healthcare providers and at least two healthcare providers of said plurality have different medical record systems.

38. The method of claim 17 wherein access to a stored categorized electronic image in said storage area is under control of said patient.

39. A method for a patient accessing said patient's medical records originating from at least one health care provider, said method comprising:
   collecting from said healthcare provider said patient's medical records, wherein said collecting is performed by a service provider, said collecting including the steps of the service provider contacting said healthcare provider to request said patient's medical records and the service provider receiving said patient's medical records from said healthcare provider;
   categorizing electronic images of said patient's medical records according to a standard set of categories, wherein said categorizing includes categorizing each electronic image of the patient's collected medical records;
   storing in a storage area of a computer said categorized electronic images, wherein said storage area comprises a database; and
   displaying a log of said categorized electronic images.

40. The method of claim 39 further comprising displaying a time line graph indicating a date when an electronic image of said categorized electronic images was created.

41. The method of claim 39 wherein said log comprises an inventory of said categorized electronic images sorted by document identifier, page type, author of said record, specialization of said author, record provider, or record date.

42. The method of claim 41 wherein the document identifier comprises a document name or a document title.

43. The method of claim 39 wherein said log is sorted by date in reverse chronological order.

44. The method of claim 39 wherein said log comprises a link to display an electronic image.

45. The method of claim 39 wherein the patient identifies the healthcare provider to the service provider and wherein the collecting is at the request of the patient.

46. The method of claim 39 wherein access to said categorized electronic images in said storage area is under the control of said patient.

47. A system for centrally managing medical records of a patient from at least one healthcare provider, said system comprising:
   a collection module for collecting from said healthcare provider said medical records, wherein a service provider contacts said healthcare provider to request said medical records and receives said medical records from said healthcare provider, and wherein said collection module is other than the patient;
   a computerized system for categorizing each medical record into a standard set of categories;
   a storage area wherein said storage area comprises a database for electronically storing categorized electronic images of said categorized medical records; and
   a retrieval module for retrieving an ordered set of electronic images of said categorized electronic images, wherein said ordered set of electronic images is arranged using at least one of a plurality of criteria, said plurality of criteria based on said computerized system.

48. The system of claim 47 further comprising a display for displaying said ordered set of electronic images.

49. The system of claim 48 wherein said display for presenting comprises a Web browser.

50. The system of claim 47 further comprising a distribution module for creating a CD, email, facsimile document, or printed document comprising information in said ordered set of electronic images.

51. The system of claim 47 further comprising a search engine application stored in a computer readable medium for locating a doctor or an organization of said healthcare provider.

52. The system of claim 47 wherein said computerized system for categorizing each medical record comprises: document identifier, page type, author of said record, specialization of said author, provider of the record, and date of the record.

53. The method of claim 52 wherein the document identifier comprises a document name or a document title.

54. The system of claim 47 wherein the medical records of the patient are distributed across a plurality of health care providers.

55. The system of claim 47 wherein the patient identifies the plurality of healthcare providers to the service provider, and collecting is at the request of the patient.

56. The system of claim 47 wherein said set of standard categories is the same for all healthcare providers.

57. A method of centrally managing medical records of a patient authored by at least one healthcare provider, said method comprising:
   collecting from said at least one healthcare provider medical records, wherein said medical records comprise paper based documents, and wherein said collecting is performed by a service provider;
   classifying each page of said paper based documents using classes of a classification system, the classes being a standard set of classes;
   converting each page of said paper based documents to an electronic image;
   storing each electronic image in a computer readable medium;
   retrieving an organized subset of said electronic images, using at least one of a plurality of criteria; and
   displaying an electronic image of said organized subset.

58. The method of claim 57 wherein said classifying each page comprises adding a header and a footer to each page, wherein said header comprises a first group of classes of said classification system and said footer comprises a second group of classes of said classification system.

59. The method of claim 58 wherein said first group comprises: a document identifier, page type, patient name, and member identifier.

60. The method of claim 59 wherein said page type is a medical category selected from a group comprising: Medications & Allergies, Immunizations, Patient Intake Apps, Physical Exams, Progress Notes, Consultations, Operative Notes, ER Reports, Hospital Summaries, EKGs, Imaging Reports, Special Tests, Labs & Cultures, Therapy Notes, Billing & Insurance, and Other.

61. The method of claim 59 wherein the document identifier comprises a document name or a document title.

62. The method of claim 58 wherein said second group comprises: author of said page, author's specialization, if a doctor, and creation date of said page.

63. The method of claim 57 wherein said classification system comprises: a document identifier, page type, patient name, member identifier, author of said page, author's specialization, if a doctor, and creation date of said page.

64. The method of claim 57 wherein the classes of the classification system are common across a plurality of healthcare providers.

65. The method of claim 57 wherein the patient identifies to the service provider a plurality of healthcare providers from which medical records are to be collected.

66. The method of claim 57 wherein access to said computer readable medium is authorized by said patient.

67. The method of claim 57 wherein said at least one healthcare provider comprises a past and a current health care provider.

68. A system for centrally managing a medical records of a patient originating from at least one healthcare provider, said system comprising:
   a backend server for receiving said medical records from said at least one healthcare provider, wherein each document of said medical records is categorized into a standard set of categories, wherein said plurality of medical records are collected by a service provider, wherein the service provider contacts said healthcare provider to request said medical records and the service provider receives said medical records from said healthcare provider;
   a database connected to said backend server for storing said categorized documents as electronic images; and
   a Web server connected to said backend server and to a client system, wherein said Web server processes a search request by said client system for retrieving a set of ordered documents of said categorized documents, said set arranged by using at least one of a plurality of criteria.

69. The system of claim 68 further comprising a scanner coupled to said backend server for converting a paper-based document of said medical records to an electronic image for storing in said database.

70. The system of claim 68 further comprising a search engine for locating the at least one a healthcare provider.

71. The system of claim 68 further comprising a window displaying a current collection status of a patient's medical records from the at least one healthcare provider.

72. The system of claim 68 wherein the patient identifies the healthcare provider to the service provider.

73. The system of claim 68 wherein collecting of the medical records by the service provider is in response to a request by the patient.

74. The system of claim 68 wherein access to said categorized documents is controlled by said patient.

75. A method for a service provider to manage a patient's medical records authored by a plurality of healthcare providers, said method comprising:
   the service provider:
      collecting the patient's medical records from each of the plurality of healthcare providers;
      making an electronic image of each document in the collected patient's medical records;
      categorizing the electronic images according to a standard set of categories;
      storing in a data base in a computer storage the categorized electronic images; and
      retrieving from said computer storage an ordered set of electronic images of the categorized electronic images, using at least one of a plurality of predetermined criteria.

76. The method of claim 75 wherein said plurality of predetermined criteria include sorting said categorized electronic images in reverse chronological order of creation dates, by medical sub-category, by author, by author specialization, in numerical order of document identifier, by document provider, or any combination thereof.

77. The method of claim 75 further comprising:
sorting said plurality of electronic images; and
presenting said sorted plurality of electronic images based on a selection criterion and a prioritization algorithm.

78. The method of claim 75 further comprising providing said ordered set of electronic images to a healthcare provider examining said patient.

79. The method of claim 78 wherein said providing said ordered set of electronic images to a healthcare provider occurs only for electronic images in said ordered set which are not marked private by said patient.

80. The method of claim 75 wherein said standard set of categories is the same for all healthcare providers of said plurality of healthcare providers.

81. The method of claim 75 wherein said standard set of categories comprises a plurality of categories, said categories comprising a document identifier.

82. The method of claim 81 wherein said categories further comprise: an author of a page, a specialization of said author, a date said page was created, a page type, a record source, or a name of a file provider.

83. The method of claim 75 wherein said plurality of electronic images comprises scanned paper-based pages of said patient's medical records.

84. The method of claim 75 further comprising:
the service provider automatically generating letters for said patient's signature to request said plurality of electronic images of said patient's medical records.

85. The method of claim 75 further comprising displaying a log of said categorized plurality of electronic images to said patient.

86. The method of claim 75 wherein at least two healthcare providers of said plurality of healthcare providers have different medical record systems.

87. The method of claim 75 further comprising displaying said retrieved electronic images to said patient, a third party after approval by said patient, or to said patient's legal surrogate, or any combination thereof.

88. The method of claim 75 further comprising distributing said retrieved document by fax, email, or hard copy.

89. The method of claim 75 wherein said hard copy comprises a floppy disk, CD, microfiche, or paper copy.

90. The method of claim 75 wherein said standard set of categories is used by all healthcare providers of said plurality of healthcare providers.

91. The method of claim 75 further comprising the service provider obtaining authorization from the patient to collect the patient's medical records from each of the plurality of healthcare providers.

92. The method of claim 75 further comprising the service provider obtaining authorization from the patient for access to said categorized electronic images.

* * * * *